(12) United States Patent
Zupancic

(10) Patent No.: US 8,349,980 B2
(45) Date of Patent: Jan. 8, 2013

(54) BIO-BASED POLYOL

(75) Inventor: Joseph James Zupancic, Glen Ellyn, IL (US)

(73) Assignee: Rohm and Haas Company, Philadelphia, PA (US)

(*) Notice: Subject to any disclaimer, the term of this patent is extended or adjusted under 35 U.S.C. 154(b) by 300 days.

(21) Appl. No.: 12/710,632

(22) Filed: Feb. 23, 2010

(65) Prior Publication Data

US 2010/0222541 A1    Sep. 2, 2010

Related U.S. Application Data

(60) Provisional application No. 61/208,936, filed on Mar. 2, 2009.

(51) Int. Cl.
| | |
|---|---|
| C08F 120/20 | (2006.01) |
| C08F 122/00 | (2006.01) |
| C08G 4/00 | (2006.01) |

(52) U.S. Cl. .................. 526/318; 526/317.1; 526/318.1; 526/318.2; 526/72; 528/230; 528/245.3; 528/74.5

(58) Field of Classification Search .................. None
See application file for complete search history.

(56) References Cited

U.S. PATENT DOCUMENTS

| | | | |
|---|---|---|---|
| 2,188,882 | A | 1/1940 | Clocker |
| 2,569,420 | A | 9/1951 | Kosmin |
| 6,121,398 | A | 9/2000 | Wool et al. |
| 2007/0276121 | A1 | 11/2007 | Westerfom et al. |

FOREIGN PATENT DOCUMENTS

| | | |
|---|---|---|
| DE | 635926 | 9/1936 |
| JP | 48045620 A | 6/1973 |
| JP | 2004238763 A | 8/2004 |
| PL | 189376 | * 7/2005 |

OTHER PUBLICATIONS

Ostrysz, R. et al., Productin of vegetable oil-based polyester-polyols suitable for production of stiff polyurethane foams, 2005, English translation of Abstract, pp. 1.*

Khot, et al., "Development and Application of Triglyceride-Based Polymers and Composites", J. Applied Polymer Science, vol. 82, pp. 703-723 (2001).

Quesada, et al., "Preparation of Alkenyl Succinic Anhydrides from Vegetable Oil FAME", JAOCS, vol. 80, No. 3, pp. 281-286 (2003).

Bickford, et al, "The Reaction of Nonconjugated Unsaturated Fatty Acid Esters With Maleic Anhydride", Oil & Soap, vol. 19, pp. 23-27 (1942).

Eren, et al., "Polymerization of Maleic Anhydride-Modified Plant Oils with Polyols", J. Applied Polymer Science, vol. 90, pp. 197-202 (2003).

* cited by examiner

*Primary Examiner* — Yate K Cutliff
(74) *Attorney, Agent, or Firm* — Kenneth Crimaldi

(57) ABSTRACT

A polyol having a substituent of formula (I)

$$R^1O-\underset{\underset{O}{\|}}{C}-\underset{H_2}{C}-\underset{|}{CH}-\underset{\|}{C}-OR^2 \quad (I)$$

attached via a carbon-carbon single bond to a saturated carbon atom in a fatty acid hydrocarbyl group; wherein $R^1$ and $R^2$ are esterified residues of aliphatic or cycloaliphatic diols; and from 0 to 15 wt % of esterified residues of at least one $C_4$-$C_{12}$ anhydride, $C_4$-$C_{12}$ diacid or $C_4$-$C_{12}$ lactone, not including units of formula (I) attached to a fatty acid hydrocarbyl group.

4 Claims, No Drawings

BIO-BASED POLYOL

This application claims the benefit of priority under 35 U.S.C. §119(e) of U.S. Provisional Patent Application No. 61/208,936 filed on Mar. 2, 2009.

BACKGROUND

This invention relates generally to a polyol produced from biological materials.

The use of triglycerides in preparation of alkyd resins is well known. Typically, these resins are produced without modifying the fatty acid chains, but rather by utilizing the triglyceride ester groups to react with acids and glycols to form polyesters. Such resins usually have high molecular weights and require solvent to deliver the resin in a coating application.

Production of condensation products useful in paints from reaction of triglycerides with maleic anhydride, followed by reaction with ethylene glycol has been described. For example, U.S. Pat. No. 2,188,882 to Clocker discloses the reaction of linseed oil with 10% by weight maleic anhydride at 250° C., followed by reaction of the product with a small amount of ethylene glycol at about 180° C. However, the material produced in this way is extremely viscous and must be dispersed in a solvent to be used. A hydroxy-functional material derived from biological materials which has a relatively low viscosity and is useable in a solvent-free composition would be a desirable product.

STATEMENT OF INVENTION

The present invention is directed to a polyol comprising a substituent of formula (I)

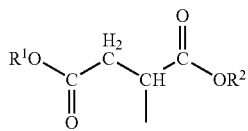

attached via a carbon-carbon single bond (shown attached to the "CH" group in formula I) to a saturated carbon atom in a fatty acid hydrocarbyl group; wherein $R^1$ and $R^2$ are esterified residues of aliphatic or cycloaliphatic diols; and wherein the polyol comprises: (i) from 0.36 to 0.48 units of formula (I) per fatty acid hydrocarbyl group, and (ii) from 0 to 10 wt % of esterified residues of at least one $C_4$-$C_{12}$ anhydride, $C_4$-$C_{12}$ diacid or $C_4$-$C_{12}$ lactone, not including units of formula (I) attached to a fatty acid hydrocarbyl group; and wherein the polyol has a hydroxyl number from 100 to 225 mg KOH/g.

The present invention is further directed to a method for making the polyol. The method comprises the following steps: (a) allowing a triglyceride having a saturated fat content no greater than 29 wt % to react with 0.12 to 0.16 g maleic anhydride/g triglyceride at a temperature from 150° C. to 250° C. to form a maleated triglyceride; and (b) allowing the maleated triglyceride to react with at least one $C_2$-$C_{40}$ aliphatic or cycloaliphatic diol and up to 15 wt % of at least one $C_4$-$C_{12}$ anhydride, $C_4$-$C_{12}$ diacid or $C_4$-$C_{12}$ lactone, based on total weight of ingredients from both steps, at a temperature from 170° C. to 260° C.

DETAILED DESCRIPTION

All percentages are weight percentages, and all temperatures are in ° C., unless otherwise indicated. "Triglycerides" used in this invention are natural fats or oils comprising glycerine triesters of fatty acids. Preferably, triglycerides are in the form of vegetable oils, but animal fats can also be used as a starting material if they have sufficiently low saturated fatty acid content. Fatty acids are acyclic aliphatic carboxylic acids containing from 8 to 22 carbon atoms; typically, they contain from 12 to 22 carbon atoms. In most natural triglycerides, at least 95% of the fatty acid residues have from 16 to 18 carbon atoms. With respect to carbon-carbon bonds, the fatty acids may be saturated, monounsaturated or polyunsaturated (typically 2 or 3 carbon-carbon double bonds). The "fatty acid hydrocarbyl group" is the alkyl or alkenyl chain attached to the carboxylic acid group. Natural fats may also contain small amounts of other esterified, or free fatty acids, as well as small amounts (1-4%) of phospholipids, e.g., lecithin, and very small amounts (<1%) of other compounds, e.g., tocopherols. Preferably, the free fatty acid content of the triglyceride is no greater than 10%, alternatively no greater than 5%, alternatively no greater than 3%. Triglycerides suitable for use in this invention have a saturated fat content of no greater than 29%, alternatively no greater than 27%, alternatively no greater than 25%, alternatively no greater than 23%, alternatively no greater than 20%, alternatively no greater than 17%, alternatively no greater than 16%. The saturated fat content of triglycerides is the weight percent of fatty acid chains in the triglyceride that are saturated, normalized to 100%. Preferred triglycerides include soybean oil, corn oil, sunflower oil, canola oil, hempseed oil, flaxseed oil, olive oil, peanut oil, safflower oil and cottonseed oil. More preferred triglycerides include soybean oil, corn oil, sunflower oil, canola oil, hempseed oil, flaxseed oil, olive oil, peanut oil and safflower oil. Particularly preferred triglycerides include soybean oil, corn oil, sunflower oil, canola oil, hempseed oil, flaxseed oil, olive oil and safflower oil. The triglyceride can be isolated from naturally occurring seed sources or from genetically modified seed sources which may have enhanced levels of certain fatty acids, e.g., monounsaturated fatty acids or conjugated polyunsaturated fatty acids.

The polyol of this invention contains polymerized and esterified residues of maleic anhydride, as depicted in formula (I), attached to fatty acid hydrocarbyl groups. The fatty acid hydrocarbyl group can be designated as "R" in the following formula of a fatty acid ester: $RCO_2R^3$; wherein $R^3$ is an esterified residue of a diol, and R is a fatty acid hydrocarbyl group having from 15 to 17 carbon atoms. The structure shown here below shows the attachment of the esterified maleic anhydride residue to the fatty acid hydrocarbyl group at a CH group adjacent to a carbon-carbon double bond.

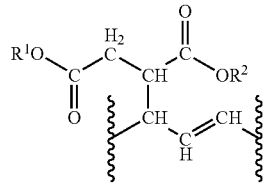

The esterified maleic anhydride residues are present in an amount of at least 0.36 units per fatty acid hydrocarbyl group; alternatively at least 0.37, alternatively at least 0.38, alternatively at least 0.39; alternatively no more than 0.47, alternatively no more than 0.46, alternatively no more than 0.45, alternatively no more than 0.44, alternatively no more than 0.43, alternatively no more than 0.42. The number of units of maleic anhydride residue per fatty acid hydrocarbyl group can be calculated from the number of moles of maleic anhydride divided by the number of moles of unsaturated fatty acid chains in the triglyceride. This number also can be determined experimentally by methods used for structure determination, e.g., $^1$H or $^{13}$C NMR. The polyol is a hydroxy-terminated polyester, preferably with a hydroxyl number from 100 to 225 mg KOH/g, alternatively from 125 to 200, alternatively from 150 to 195. Preferably, the viscosity of the polyol at 25° C. is from 100 to 5000 cps (100 to 5000 mPa·s), alternatively from 500 to 3500 cps (500 to 3500 mPa·s). In some embodiments of the invention, the polyol contains from 10% to 40% polymerized residues of at least one $C_2$-$C_{40}$ aliphatic or cycloaliphatic diol; alternatively at least 17%, alternatively at least 20%, alternatively at least 22%, alternatively at least 24%; alternatively no more than 35%, alternatively no more than 33%, alternatively no more than 31%, alternatively no more than 29%, alternatively no more than 27%, alternatively no more than 25%. In some embodiments of the invention, the polyol contains from 1.0 to 1.8 moles of diol residues per mole of polyol; alternatively at least 1.1 moles, alternatively at least 1.2 moles; alternatively no more than 1.6 moles, alternatively no more than 1.55 moles. Preferably, the $C_2$-$C_{40}$ diol is is selected from the group consisting of ethylene glycol, diethylene glycol, triethylene glycol, polyethylene glycol (maximum Mn=400), propylene glycol, dipropylene glycol, polypropylene glycol (maximum Mn=400), 1,4-butanediol, 2-methyl-1,3-propanediol, neopentyl glycol, 1,4-dimethanol-cyclohexane and 1,6-hexanediol. Small amounts of residues of compounds with more than three hydroxy groups may be present to increase branching, e.g., pentaerythritol. Preferably, the amount of residues of compounds with more than three hydroxy groups is no more than 0.5% of the total amount of diol(s), alternatively no more than 0.3%, alternatively no more than 0.2%, alternatively no more than 0.1%. In some embodiments of the invention, the $C_2$-$C_{40}$ diol is an aliphatic $C_2$-$C_8$ diol, alternatively a $C_2$-$C_6$ diol, alternatively a $C_2$-$C_4$ diol. In some embodiments of the invention, the amount of triol residues present in excess of the amount due to glycerol from the triglyceride is no more than 2% of the total amount of diol and triol residues in excess of the amount due to glycerol from the triglyceride, alternatively no more than 1%, alternatively no more than 0.5%, alternatively no more than 0.3%, alternatively no more than 0.1%. Suitable triols include, e.g., glycerol, trimethylol ethane and trimethylol propane.

The maleic anhydride reacts with the unsaturated triglyceride chains to form a carbon-carbon bond. Without being bound to theory, it is believed that maleic anhydride reacts with the unsaturated fatty acid hydrocarbyl groups via an Alder Ene reaction, as depicted below for an oleate chain of a triglyceride.

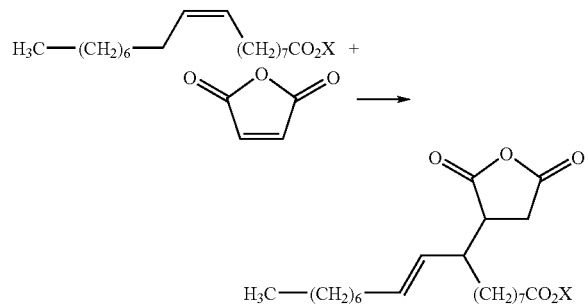

Only one of two possible isomeric products is shown. "X" represents the remaining part of the triglyceride which contains the oleate chain. The same reaction may occur on other unsaturated fatty acid chains in the same triglyceride molecule. Subsequent reaction of this product with $C_2$-$C_{40}$ diol(s) opens and esterifies the anhydride, and also is capable of transesterifying the triglyceride to form a fatty acid ester with a group of formula (I) attached to a $CH_2$ group in the fatty acid hydrocarbyl group, as illustrated below for the case where the $C_2$-$C_{40}$ diol is ethylene glycol.

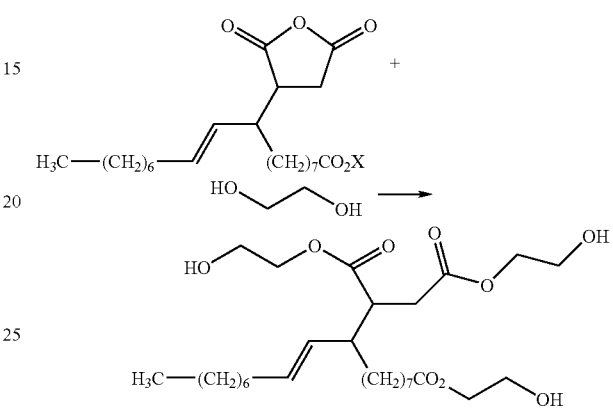

Of course glycerol liberated by transesterification of the triglyceride will esterify acid groups to form some species more branched than that shown above, and there will also be esterified saturated fatty acids, and other species in a complex mixture. It is possible that a fatty acid hydrocarbyl group bearing an esterified maleic anhydride moiety still may be attached to an incompletely transesterified triglyceride, as shown below

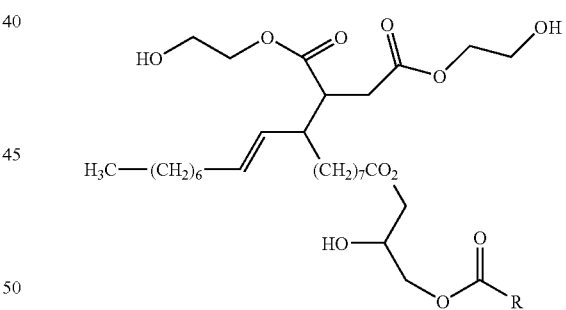

where R represents a fatty acid hydrocarbyl group which may be substituted by an esterified maleic anhydride. The free hydroxyl groups present in the various species may react with anhydride functionality on other chains, or if present, added anhydrides or diacids, and then with additional diol/triol, including glycerol from the triglyceride, generating a hydroxy-terminated polyester substituent. Preferably, in preparation of the polyol, the $C_2$-$C_{40}$ diol or triol is added in sufficient amount to react with all anhydride or carboxylic acid functionality, thereby producing a polyol which is a hydroxy-terminated polyester with a low acid number, preferably less than 15 mg KOH/g, more preferably less than 10, most preferably less than 5.

In unusual cases where the double bonds in a polyunsaturated fatty acid chain have isomerized to become a conjugated 1,4-diene, it is possible for the maleic anhydride to undergo a Diels-Alder cycloaddition reaction with the diene to form a cyclohexene structure. The isomerization may result from chemically induced isomerization or be produced in a genetically modified organism. However, even in such cases, the predominant product of maleic anhydride addition is as shown above.

The polyol further comprises polymerized residues of a $C_4$-$C_{12}$ anhydride, $C_4$-$C_{12}$ diacid or $C_4$-$C_{12}$ lactone in an amount from 0 to 15% (not including the amount stated above for maleic anhydride residues, which is approximately 8 to 15%); alternatively the anhydride, diacid or lactone amount is at least 1%, alternatively at least 2%, alternatively at least 3%, alternatively at least 4%; alternatively no more than 12%, alternatively no more than 10%, alternatively no more than 9%, alternatively no more than 8%, alternatively no more than 7%, alternatively no more than 6%. In some embodiments of the invention, the $C_4$-$C_{12}$ anhydride, diacid or lactone is a $C_4$-$C_{10}$ anhydride or diacid. In some embodiments of the invention, it is selected from the group consisting of adipic acid, azelaic acid, succinic acid, sebacic acid, fumaric acid, maleic acid, phthalic anhydride, isophthalic acid, terephthalic acid, maleic anhydride, succinic anhydride, tetrahydrophthalic anhydride, hexahydrophthalic anhydride and caprolactone. In some embodiments of the invention, the $C_4$-$C_{12}$ anhydride, diacid or lactone is a $C_8$-$C_{12}$ aromatic anhydride or diacid, alternatively a $C_8$-$C_{10}$ aromatic anhydride or diacid. The product illustrated above, derived from maleic-anydride-modified oleic acid and ethylene glycol, would be expected to react further on some or all available hydroxyl groups to give a structure like the one shown below for reaction with phthalic anhydride

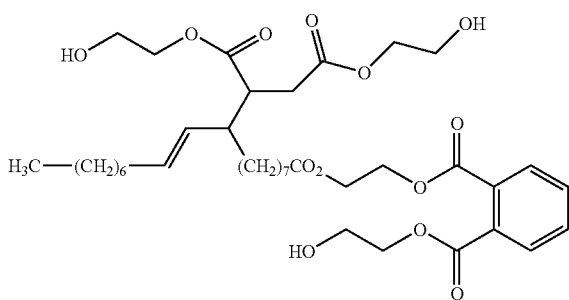

The polyol is produced by the steps of (a) allowing the triglyceride to react with 0.12 to 0.16 g maleic anhydride/g triglyceride at a temperature from 150° C. to 250° C. to form a maleated triglyceride; and (b) allowing the maleated triglyceride to react with at least one $C_2$-$C_{40}$ diol and 0 to 15 wt % of at least one $C_4$-$C_{12}$ anhydride, $C_4$-$C_{12}$ diacid or $C_4$-$C_{12}$ lactone (this amount does not include maleic anhydride from step (a), now part of the maleated triglyceride), based on total weight of ingredients from both steps, (a) and (b), at a temperature from 170° C. to 260° C. In some embodiments of the invention, the reaction temperature in step (a) is from 180° C. to 235° C., alternatively from 190° C. to 230° C. In some embodiments of the invention, the reaction pressure is from about atmospheric pressure (about 100 kPa) to 1750 kPa, alternatively at least 200 kPa, alternatively at least 300 kPa, alternatively no more than 700 kPa. In some embodiments of the invention, the reaction temperature in step (b) is from 180° C. to 250° C., alternatively from 190° C. to 240° C. In some embodiments of the invention, the reaction mixture is cooled below 100° C. after step (a) to control the exothermic initial reaction in step (b), and then reheated to the indicated reaction temperature. Reaction times of course will vary with the other conditions, and can be determined easily by one skilled in the art, but typically are in the range from 1 hour to 10 hours, alternatively from 2 to 8 hours. Preferably, an esterification/transesterification catalyst is present during step (b) in an amount no more than 0.1 wt %, alternatively 0.01 wt %. These catalysts are well known in the art and include tin, titanium, bismuth and zirconium catalysts. Tin catalysts are preferred, especially alkyltin tris-alkanoates, hydroxybutyl tin oxide, tetra-alkoxy titanates and bismuth alkanoates. In some embodiments of the invention, 1 wt % to 15 wt % of a $C_4$-$C_{12}$ anhydride, diacid or lactone is added in step (b), alternatively 1 wt % to 9 wt %. Preferably, the anhydride, diacid or lactone is added to the maleated triglyceride at approximately the same time as the $C_2$-$C_{40}$ diol(s) (and triol(s), if used). In some embodiments of the invention, the anhydride, diacid or lactone is added slightly before the diol(s) to allow good mixing with the maleated triglyceride prior to the esterification/transesterification reactions with the diol(s) and triol(s), i.e., no more than 60 minutes prior to anhydride/diacid addition, alternatively no more than 30 minutes, alternatively no more than 20 minutes, alternatively no more than 10 minutes.

In some embodiments of the invention, the triglyceride is allowed to react with at least 0.125 g maleic anhydride/g triglyceride, alternatively at least 0.13 g; alternatively no more than 0.155 g, alternatively no more than 0.15 g, alternatively no more than 0.145 g, alternatively no more than 0.14 g.

In some embodiments of the invention, the amount of $C_2$-$C_{40}$ diol(s) is from 10% to 40%, based on total ingredients in the reaction mixture; alternatively at least 17%, alternatively at least 20%, alternatively at least 22%, alternatively at least 24%; alternatively no more than 35%, alternatively no more than 33%, alternatively no more than 31%, alternatively no more than 29%. In some embodiments of the invention, the reaction mixture contains from 1.0 to 1.8 moles of diol per moles of total ingredients; alternatively at least 1.1 moles, alternatively at least 1.2 moles; alternatively no more than 1.6 moles, alternatively no more than 1.55 moles. In some embodiments of the invention, at least one triol also is present in an amount no more than 2% of the total amount of diols and triols, alternatively no more than 1%, alternatively no more than 0.5%, alternatively no more than 0.3%, alternatively no more than 0.2%. Small amounts of compounds with more than three hydroxy groups may be added to increase branching, e.g., pentaerythritol. Preferably, the amount of compounds with more than three hydroxy groups is no more than 0.5% of the total amount of diols and trials, alternatively no more than 0.3%, alternatively no more than 0.2%, alternatively no more than 0.1%. In some embodiments of the invention, the reactants added to the reaction mixture in step (b) are substantially free of triols and higher-functional hydroxy compounds, i.e., only diols are added. Preferably, the amount of diols, trials, and tetra-ols added is sufficient to react with all of the carboxyl functionalities and to result in a polyol with a hydroxyl number from 100 to 225, alternatively from 125 to 200, alternatively from 150 to 195. This amount can be calculated easily from the amounts of other ingredients.

In some embodiments of the invention, the amount of $C_4$-$C_{12}$ anhydride, diacid or lactone, based on total weight of ingredients in both steps, is at least 1%, alternatively at least 2%, alternatively at least 3%; alternatively at least 4%, alternatively no more than 10%, alternatively no more than 9%, alternatively no more than 8%, alternatively no more than 7%.

In some embodiments of the invention, a small amount of a mono-functional hydroxy-reactive compound is added to the reaction along with diol/anhydride/lactone to decrease hydroxyl functionality and, possibly, to limit molecular weight and viscosity. Carboxylic acids are suitable for this purpose, e.g., $C_7$-$C_{22}$ carboxylic acids, alternatively $C_7$-$C_{14}$ carboxylic acids, alternatively $C_7$-$C_{10}$ carboxylic acids. Aromatic carboxylic acids are preferred. Preferably, these compounds do not have hydroxyl or amino functional groups. The amount of such compounds that may be added is from 3% to 10% of the total ingredients; alternatively at least 4%, alternatively at least 5%; alternatively no more than 8%, alternatively no more than 6%. Particularly preferred compounds include, e.g., benzoic acid and octanoic acid.

In some embodiments of the invention, the polyol is used as part of a two-component solventless adhesive system in which one component comprises the polyol and the other an isocyanate-terminated prepolymer. The isocyanate-terminated prepolymer has polymerized residues of at least one difunctional aromatic isocyanate. Either a polyisocyanate or another isocyanate-terminated prepolymer can be employed to make the isocyanate-terminated prepolymer. When a polyisocyanate is employed, it may be an aromatic diisocyanate, e.g., toluene diisocyanate (TDI), diphenyl methane diisocyanate (MDI), isomers thereof or mixtures thereof; or an aliphatic diisocyanate, e.g., hexamethylene diisocyanate, or a mixture thereof. Among the aromatic diisocyanates, MDI is preferred, especially a mixture of 4,4' and 2,4' isomers. Isocyanate-terminated polyurethane prepolymers of a polyisocyanate and a polyol may also be employed. The difunctional aromatic isocyanate or difunctional isocyanate-terminated prepolymer is mixed with a polyol to form the isocyanate-terminated prepolymer. In some embodiments of the invention, the polyol mixed into the isocyanate component is at least one difunctional polymer of ethylene oxide, propylene oxide or a combination thereof. Preferably, the average molecular weight (Mn) of the difunctional polyol is from 300 to 650, alternatively from 350 to 550, alternatively from 350 to 500. Preferably, the isocyanate-terminated prepolymer has an isocyanate content from 7% to 21%, more preferably from 11% to 19%. Preferably, the two-component adhesive system contains no more than 2% solvent, alternatively no more than 1%, alternatively no more than 0.5%. As the term is used herein, a solvent is a substance which is liquid at 25° C. and has a boiling point at atmospheric pressure of no more than 100° C.

In the two-component system of this invention, the relative proportions of isocyanate groups to isocyanate-reactive groups may vary as desired, preferably within a molar ratio of NCO/OH groups of 0.9:1 to 2:1. In some embodiments of the invention, the NCO/OH group molar ratio is from 1:1 to 1.8:1, alternatively from 1.1:1 to 1.6:1, alternatively from 1.2:1 to 1.5:1.

The system of the present invention contemplates the employment of two components, which preferably are mixed using a suitable mixer (e.g., an electrically, pneumatically, or an otherwise powered mechanical mixer, or a static mixer) prior to or during application to a substrate to form the bonding agent. Thus, the isocyanate component typically will be packaged separately from the polyol component. Mixing may take place at any suitable time prior to the laminating process. All of the present steps may be carried out under ambient room temperature or supra-ambient conditions. For example, the two components may be heated just prior to mixing and applied at elevated temperature during the coating and lamination process. Preferably, the temperature does not exceed 65° C. As desired, heating or cooling may be applied to the resulting laminate.

The bonding agent of the present invention is useful for bonding two to five substrates together. The substrates may be similar material or dissimilar material. In a preferred embodiment, a layer of the bonding agent is applied to a first substrate layer, and the resulting bonding agent layer is covered with a second substrate layer to form a laminated article wherein the two substrates are bonded together by the dried layer of bonding agent. A third and fourth layer of film can be added to the laminate to form three- or four-layer laminates. In a preferred embodiment, the substrate layers are provided in the form of rolls of substrate material. The sheets may be on the order of 0.5 to 10 mils in thickness. Larger thicknesses are also possible, as are smaller thicknesses (e.g., on the order of 5 or more microns).

The compositions of the present invention can be applied to desired substrates using conventional application techniques such as solvent-less laminators, rotogravure printing, flexographic printing, conventional or airless spray, roll coating, brush coating, wire wound rod coating, knife coating, or coating processes such as curtain-, flood-, bell-, disc-, and dip-coating processes. Coating with the bonding agent may be done over an entire surface or only a portion of it, such as along an edge, or at intermittent locations. The bonding agent is particularly attractive for packaging and sealing applications for laminating plastic films, metal films or metallized plastic films. Especially preferred films include low density polyethylene, high density polyethylene, polypropylene (cast, blown oriented, biaxially drawn), nylon, polystyrene, co-extruded films, polyester film, ceramic (SiOx, AlOx) coated film (polyester, nylon, etc.), polyacrylic acid-coated film (polyester, nylon, etc.), polyvinylidene chloride coated film, metallized film (polyester, polypropylene, etc.).

EXAMPLES

Viscosities were measured using a Brookfield viscometer operating at a temperature of approximately 25° C. Spindle numbers 2 and 5 were used as appropriate for the viscosity ranges measured. Polyols were prepared as described in the following procedures.

Example 1

Preparation of Bio-Based Polyester Resin (Polyol) (Comparative)

| Item | Monomer/Intermediate | Charge (g) |
| --- | --- | --- |
| 1 | Soybean Oil | 1000.90 |
| 2 | Maleic Anhydride | 222.27 |
| 3 | Ethylene Glycol | 304.77 |
| 4 | Glycerol | 0.34 |
| 5 | Butyltin tris(2-Ethyl hexanoate) | 1.23 |

1. Charge Items 1 and 2 to reactor at ambient temperature (ca. 25 C).
2. Heat resin to 200 C under Nitrogen with stirring.
3. Maintain resin at 200 C for 2 Hours, Monitor viscosity at 1 Hr intervals.
4. Cool resin to about 5 C.
5. Add Items 3, 4, and 5 to resin over 10 min interval; Maintain at 50 C for 30 mins.

6. Heat resin to 100 C and maintain at 100 C for 30 mins.
7. Heat resin to 225 C and hold at 225 C until AV≦5 (monitor AV and viscosity at 1 hr intervals).
8. When AV≦5 cool resin to ca. 150 C then filter and package.

The final resin had the following properties: Acid Value (AV) 2.58, Hydroxyl Number (OHN) 202.4, Mn 1900, Mw 66850, Viscosity at 25° C. 14425 cps (mPa·s).

Example 2

Preparation of Bio-Based Polyester Resin (Comparative)

| Item | Monomer/Intermediate | Charge (g) |
|---|---|---|
| 1 | Soybean Oil | 1004.85 |
| 2 | Maleic Anhydride | 222.92 |
| 3 | Ethylene Glycol | 284.10 |
| 4 | Glycerol | 0.38 |
| 5 | Butyltin tris(2-Ethyl hexanoate) | 0.58 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 50 C
5 Add Item 5 to reactor
6 Add Item 3 and 4 to resin over 10 min interval; Maintain at 50 C for 30 mins
7 Heat slowly to 100 and maintain for 30 mins.
8 Heat resin to 210 C and hold at 210 C for 1 Hr, monitor AV and viscosity every 1 Hr
9 Maintain resin at 210 C until AV<20
10 Cool Resin to about 150 C; Filter and Package The final resin had the following properties: Acid Value (AV) 16.4, Hydroxyl Number (OHN) 184.8, Mn 1800, Mw 36300, and Viscosity at 25° C. 8412 cps.

Example 3

Preparation of Bio-Based Polyester Resin (Comparative)

| Item | Monomer/Intermediate | Charge (g) |
|---|---|---|
| 1 | Soybean Oil | 1006.80 |
| 2 | Maleic Anhydride | 223.20 |
| 3 | Ethylene Glycol | 283.58 |
| 4 | Glycerol | 0.36 |
| 5 | Butyltin tris(2-Ethyl hexanoate) | 0.51 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 6 C
5 Add Item 5 to reactor
6 Add Item 3 and 4 to resin over 10 min interval; Maintain at 50-60 C for 30 mins
7 Heat slowly to 100 and maintain for 30 mins.
8 Heat resin to 210 C and hold at 210 C for 0.5 Hr, Monitor AV and viscosity
9 When AV<25.0 Apply vacuum (ea. 300) and hold resin at 210 C for 0.5 Hr;
10 Sample resin for AV and Viscosity; When AV<12.0 Start Cooling
11 Cool Resin to about 150 C; Filter and Package The final resin had the following properties: Acid Value (AV) 11.4, Hydroxyl Number (OHN) 172.7, Mn 2050, Mw 182100, and Viscosity at 25° C. 24000 cps.

Example 4

Preparation of Bio-Based Polyester Resin (Comparative)

| Item | Monomer/Intermediate | Charge (g) |
|---|---|---|
| 1 | Soybean Oil (Pure Vegetable Oil) | 1217.71 |
| 2 | Maleic Anhydride | 224.43 |
| 3 | Ethylene Glycol | 324.91 |
| 4 | Glycerol | 0.63 |
| 5 | Phthalic Anhydride | 101.10 |
| 6 | (FASCAT 4102) Butyltin tris(2-Ethylhexanoate) | 0.71 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at less than 80 C Add Item # 5 and 6; Continue cooling to 65 C
6 When resin is at 60 C Add Item # 3 and 4; Maintain at 60-65 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<5
10 Cool Resin to about 150 C; Filter and Package The final resin had the following properties: Acid Value (AV) 7.1, Hydroxyl Number (OHN) 154, Mn 1500, Mw 34500, and Viscosity at 25° C. 8875 cps.

Example 5

Preparation of Bio-Based Polyester Resin (Comparative)

| Item | Monomer/Intermediate | Charge (g) |
|---|---|---|
| 1 | Soybean Oil (Pure Vegetable Oil) | 1217.51 |
| 2 | Maleic Anhydride | 225.39 |
| 3 | Ethylene Glycol | 368.94 |
| 4 | Glycerol | 0.61 |
| 5 | Phthalic Anhydride | 102.09 |
| 6 | (FASCAT 4102) Butyltin tris(2-Ethylhexanoate) | 0.71 |

1 Charge Items 1-2 to vessel at Ambient Temperature (25-30 C)
2 Heat resin to 200 C under Nitrogen with stirring 3 Maintain resin at 200 C for 2 Hours, Monitor viscosity every 1 Hr
4 Cool Resin to about 65 C
5 When Resin is at less than 85 C Add Item # 5 and 6; Continue cooling to 65 C
6 When resin is at 65 C Add Item # 3 and 4; Maintain at 65-70 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<5
10 Cool Resin to about 150 C; Filter and Package The final resin had the following properties: Acid Value (AV) 4.1, Hydroxyl Number (OHN) 186, Mn 1400, Mw 12150, and Viscosity at 25° C. 6888 cps.

Example 6

Preparation of Bio-Based Polyester Resin

| Item | Monomer/Intermediate | Charge (g) |
| --- | --- | --- |
| 1 | Soybean Oil (Pure Vegetable Oil) | 1224.47 |
| 2 | Maleic Anhydride | 165.60 |
| 3 | Ethylene Glycol | 321.99 |
| 4 | Glycerol | 0.64 |
| 5 | Phthalic Anhydride | 102.11 |
| 6 | (FASCAT 4102) Butyltin tris(2-Ethylhexanoate) | 0.74 |

1 Charge Items 1-2 to vessel at Ambient Temperature (25-30 C)
2 Heat resin to 200 C under Nitrogen with stirring
3 Maintain resin at 200 C for 2 Hours, Monitor In-Process Viscosity every 1 Hr
4 Cool Resin to about 65 C
5 When Resin is at less than 85 C Add Item # 5 and 6; Continue cooling to 65 C
6 When resin is at 65 C Add Item # 3 and 4; Maintain at 65-70 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<5
10 Cool Resin to about 150 C; Filter and Package The final resin had the following properties: Acid Value (AV) 2.2, Hydroxyl Number (OHN) 189, Mn 1150, Mw 5450, and Viscosity at 25° C. 1600 cps.

Example 7

Preparation of Bio-Based Polyester Resin

| Item | Monomer/Intermediate | Charge (g) |
| --- | --- | --- |
| 1 | Soybean Oil (Pure Vegetable Oil) | 1224.29 |
| 2 | Maleic Anhydride | 166.22 |
| 3 | Ethylene Glycol | 320.65 |
| 4 | Glycerol | 0.77 |
| 5 | Phthalic Anhydride | 140.54 |
| 6 | (FASCAT 4102) Butyltin tris(2-Ethylhexanoate) | 0.82 |

1 Charge Items 1-2 to vessel at Ambient Temperature (25-30 C)
2 Heat resin to 200 C under Nitrogen with stirring
3 Maintain resin at 200 C for 2 Hours, Monitor In-Process Viscosity every 1 Hr
4 Cool Resin to about 65 C
5 When Resin is at less than 85 C Add Item # 5 and 6; Continue cooling to 65 C
6 When resin is at 65 C Add Item # 3 and 4; Maintain at 65-70 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<5
10 Cool Resin to about 150 C; Filter and Package The final resin had the following properties: Acid Value (AV) 4.2, Hydroxyl Number (OHN) 167, Mn 1200, Mw 6600, and Viscosity at 25° C. 2192 cps.

Example 8

Preparation of Bio-Based Polyester Resin (Comparative)

| Item | Monomer/Intermediate | Charge (g) |
| --- | --- | --- |
| 1 | Soybean Oil (Pure Vegetable Oil) | 1218.82 |
| 2 | Maleic Anhydride | 210.07 |
| 3 | Diethylene Glycol | 625.85 |
| 4 | Glycerin | 0.58 |
| 5 | Phthalic Anhydride | 70.85 |
| 6 | (FASCAT 4102) Butyltin tris(2-Ethylhexanoate) | 0.74 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 5 and 6; Continue cooling to 65 C
6 When resin is at 65 C Add Item # 3 and 4; Maintain at 65-70 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply Vacuum; Maintain at 225 C and ca. 300 mm until AV<5
11 Cool Resin to about 150 C; Filter and Package The final resin had the following properties: Acid Value (AV) 3.2, Hydroxyl Number (OHN) 187, Mn 1600, Mw 21450, and Viscosity at 25° C. 2261.67 cps.

Example 9

Preparation of Bio-Based Polyester Resin (Comparative)

| Item | Monomer/Intermediate | Charge (g) |
|---|---|---|
| 1 | Soybean Oil (Pure Vegetable Oil) | 1225.52 |
| 2 | Maleic Anhydride | 226.53 |
| 3 | Diethylene Glycol | 689.90 |
| 4 | Pentaerythritol | 0.63 |
| 5 | Phthalic Anhydride | 103.07 |
| 6 | (FASCAT 4102) Butyltin tris(2-Ethylhexanoate) | 0.95 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 4, 5 and 6; Continue cooling to 65 C
6 When resin is at 65 C Add Item # 3; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply Vacuum; Maintain at 225 C and ca. 240 mm until AV<5
11 Cool Resin to about 150 C; Filter and Package The final resin had the following properties: Acid Value (AV) 3.8, Hydroxyl Number (OHN) 185, Mn 1800, Mw 24600, and Viscosity at 25° C. 3341.33 cps.

Example 10

Preparation of Bio-Based Polyester Resin (Comparative)

| Item | Monomer/Intermediate | Charge (g) |
|---|---|---|
| 1 | Soybean Oil (Pure Vegetable Oil) | 1220.13 |
| 2 | Maleic Anhydride | 210.42 |
| 3 | Diethylene Glycol | 463.36 |
| 4 | Ethylene Glycol | 112.10 |
| 5 | Glycerin | 0.73 |
| 6 | Phthalic Anhydride | 71.15 |
| 7 | (FASCAT 4102) Butyltin tris(2-Ethylhexanoate) | 0.79 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 5, 6 and 7; Continue cooling to 65 C
6 When resin is at 65 C Add Item # 3 and 4; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply Vacuum; Maintain at 225 C and ca. 200 mm until AV<5
11 Cool Resin to about 150 C; Filter and Package The final resin had the following properties: Acid Value (AV) 1.4, Hydroxyl Number (OHN) 181, Mn 1500, Mw 18250, and Viscosity at 25° C. 2680 cps.

Example 11

Preparation of Bio-Based Polyester Resin (Comparative)

| Item | Monomer/Intermediate | Charge (g) |
|---|---|---|
| 1 | Soybean Oil (Pure Vegetable Oil) | 1219.55 |
| 2 | Maleic Anhydride | 211.10 |
| 3 | Diethylene Glycol | 627.04 |
| 4 | Pentaerythritol | 0.69 |
| 5 | Phthalic Anhydride | 71.07 |
| 6 | (FASCAT 4102) Butyltin tris(2-Ethylhexanoate) | 0.75 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 4, 5 and 6; Continue cooling to 65 C
6 When resin is at 65 C Add Item # 3; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply Vacuum; Maintain at 225 C and ca. 200 mm until AV<5
11 Cool Resin to about 150 C; Filter and Package The final resin had the following properties: Acid Value (AV) 3.6, Hydroxyl Number (OHN) 182, Mn 1500, Mw 8700, and Viscosity at 25° C. 1938 cps.

Example 12

Preparation of Bio-Based Polyester Resin (Comparative)

| Item | Monomer/Intermediate | Charge (g) |
|---|---|---|
| 1 | Soybean Oil (Pure Vegetable Oil) | 1202.90 |
| 2 | Maleic Anhydride | 133.91 |
| 3 | Ethylene Glycol | 238.76 |
| 4 | (FASCAT 4102) Butyltin tris(2-Ethylhexanoate) | 0.75 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr 4 Cool Resin to about 65 C
5 When Resin is at 85 C Add Item # 4; Continue cooling to 65 C
6 When resin is at 65 C Add Item # 3; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply Vacuum; Maintain at 225 C and ca. 330 mm until AV<5
11 Cool Resin to about 150 C; Filter and Package The final resin had the following properties: Acid Value (AV) 0.91, Hydroxyl Number (OHN) 161, Mn 1100, Mw 8750, and Viscosity at 25° C. 1190.67 cps.

Example 13

Preparation of Bio-Based Polyester Resin

| Item | Monomer/Intermediate | Charge (g) |
|---|---|---|
| 1 | Soybean Oil (Pure Vegetable Oil) | 1224.88 |
| 2 | Maleic Anhydride | 165.79 |
| 3 | Diethylene Glycol | 472.78 |
| 4 | Ethylene Glycol | 69.68 |
| 5 | Glycerin | 0.95 |
| 6 | Phthalic Anhydride | 102.45 |
| 7 | (FASCAT 4102) Butyltin tris(2-Ethylhexanoate) | 0.87 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 5, 6 and 7; Continue cooling to 65 C
6 When resin is at 65 C Add Item # 3 and 4; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
10 When AV<15 apply vacuum; maintain at 225 C and ca. 325 mm until AV<5
11 Cool Resin to about 150 C; Filter and Package The final resin had the following properties: Acid Value (AV) 2.8, Hydroxyl Number (OHN) 181, Mn 1700, Mw 12950, and Viscosity at 25° C. 1364 cps.

Example 14

Preparation of Bio-Based Polyester Resin

| Item | Monomer/Intermediate | Charge (g) |
|---|---|---|
| 1 | Soybean Oil (Pure Vegetable Oil) | 1224.67 |
| 2 | Maleic Anhydride | 156.69 |
| 3 | Diethylene Glycol | 586.77 |
| 4 | Pentaerythritol | 0.76 |
| 5 | Phthalic Anhydride | 102.19 |
| 6 | (FASCAT 4102) Butyltin tris(2-Ethylhexanoate) | 0.75 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 4, 5 and 6; Continue cooling to 65 C
6 When resin is at 65 C Add Item # 3; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
   When AV<15 apply Vacuum; Maintain at 225 C and ca. 360 mm until AV<
10 5
11 Cool Resin to about 150 C; Filter and Package The final resin had the following properties: Acid Value (AV) 1.4, Hydroxyl Number (OHN) 189, Mn 1200, Mw 6400, and Viscosity at 25° C. 860 cps.

Example 15

Preparation of Bio-Based Polyester Resin

| Item | Monomer/Intermediate | Charge (g) |
|---|---|---|
| 1 | Soybean Oil (Pure Vegetable Oil) | 1227.27 |
| 2 | Maleic Anhydride | 166.39 |
| 3 | Diethylene Glycol | 566.54 |
| 4 | Pentaerythritol | 0.72 |
| 5 | Phthalic Anhydride | 103.33 |
| 6 | FASCAT 4100 (Hydroxybutyltin oxide) | 0.23 |

1 Charge Items 1-2 to vessel at Ambient Temperature (25-30 C)
2 Heat resin to 200 C under Nitrogen with stirring
3 Maintain resin at 200 C for 2 Hours, Monitor viscosity every 1 Hr
4 Cool Resin to about 65 C
5 When Resin is at 85 C Add Item # 4, 5 and 6; Continue cooling to 65 C
6 When resin is at 65 C Add Item # 3; Maintain at 65-75 C for 0.50 Hrs.
7 Heat slowly to 100 and maintain for 30 mins.
8 Heat resin to 225 C and hold at 225 C, Monitor AV and viscosity every 1 Hr
9 Maintain resin at 225 C until AV<15
   When AV<15 apply vacuum; maintain at 225 C and ca. 200 mm until AV<
10 5
11 Cool Resin to about 150 C; Filter and Package The final resin had the following properties: Acid Value (AV) 2.1, Hydroxyl Number (OHN) 171, Mn 1100, Mw 9400, and Viscosity at 25° C. 1310 cps.

Example 16

Preparation of Bio-Based Polyester Resin

| Item | Monomer/Intermediate | Charge (g) |
|---|---|---|
| 1 | Soybean Oil (Pure Vegetable Oil) | 1227.47 |
| 2 | Maleic Anhydride | 176.34 |
| 3 | Diethylene Glycol | 580.26 |
| 4 | Pentaerythritol | 0.69 |
| 5 | Phthalic Anhydride | 102.43 |
| 6 | FASCAT 4100 (Hydroxybutyltin oxide) | 0.25 |

1 Charge Items 1-2 to vessel at Ambient Temperature (25-30 C)

2 Heat resin to 200 C under Nitrogen with stirring

3 Maintain resin at 200 C for 2 Hours, Monitor viscosity every 1 Hr

4 Cool Resin to about 65 C

5 When Resin is at 85 C Add Item # 4, 5 and 6; Continue cooling to 65 C

6 When resin is at 65 C Add Item # 3; Maintain at 65-75 C for 0.50 Hrs.

7 Heat slowly to 100 and maintain for 30 mins.

8 Heat resin to 225 C and hold at 225 C, Monitor AV and viscosity every 1 Hr

9 Maintain resin at 225 C until AV<15

When AV<15 apply vacuum; maintain at 225 C and ca. 325 mm until AV<

10 5

11 Cool Resin to about 150 C; Filter and Package

The final resin had the following properties: Acid Value (AV) 1.4, Hydroxyl Number (OHN) 174, Mn 1150, Mw 9550, and Viscosity at 25° C. 1373 cps.

The adhesion properties of the bio-based polyesters were evaluated with Isocyanate Prepolymer resins using a series of laminate constructions. These two part adhesive systems were first screened via a solvent hand casting method and then utilizing a solventless coating method for select systems on a PolyType Solventless Coater/Laminator. The following abbreviations are used for the composition of the laminate construction: PP=polypropylene; PE=polyethylene; PET=polyester; N=nylon; MPET=metallized polyester; MPP=metallized polypropylene; BF=backed foil; 3 mil PP=3 mil cast polypropylene. The following abbreviations are used to describe test results: as: adhesive split; ftr: film tear; sec: adhesive on secondary film; zip: zippery bond. Adhesion bond strengths were determined on a 25.4 mm (1 inch) wide strip of laminate on a Thwing-Albert Tensile Tester (Model QC-3A) with a 50 Newton load cell at a 10.0 cm/min rate.

Example 17

Polyester of Example 1 was evaluated with Isocyanate Pre-Polymer I (MDI-based polyurethane prepolymer composed of 50-55% isocyanate-terminated polyurethane resin, 18-20% 4,4'-MDI and 30-32% 2,4'-MDI; and having 17.9% isocyanate groups) at a mix ratio of Isocyanate Pre-Polymer I:Polyester 1 of 100:89 (molar NCO:OH, 1.33:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 194, as | 183, as | 1.12, as | 1.06. as |
| PP/PE | 340, as | 379, ftr | 1.97, as | 2.19, as |
| PET/PE | 337, as | 408, as, zip | 1.95, as | 2.36, as, zip |
| N/PE | 486, as | 676, ftr | 2.81, as | 3.92, ftr |
| MPET/PE | 72, as | 172, as | 0.42, as | 1.00, as |
| MPP/PE | 35, sec, zip | 42, sec | 0.20, sec, zip | 0.24, sec |
| MPP/PP | 109, as | 315, ftr | 0.63, as | 1.82, ftr |
| BF/3 mil PP | 197, as | 656, as, zip | 1.14, as | 3.80, as, zip |
| BF/N | 160, as | 215, as, zip | 0.93, as | 1.25, as, zip |
| N/3 mil PP | 112, as | 637, as, zip | 0.65, as | 3.69, as, zip |

Example 18

Polyester of Example 2 was evaluated with Isocyanate Pre-Polymer I (17.9% Isocyanate) at a mix ratio of Isocyanate Pre-Polymer I:Polyester 2 of 100:93 (molar NCO:OH, 1.39:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 223, as, zip | 354, ftr | 1.29, as, zip | 2.05, ftr |
| PP/PE | 516, as | 743, as, zip | 2.99, as | 4.30, as, zip |
| PET/PE | 604, as, zip | 956, ftr | 3.50, as, zip | 5.54, ftr |
| N/PE | 728, as | 926, ftr | 4.22, as | 5.36, ftr |
| MPET/PE | 263, as | 191, ftr | 1.52, as | 1.11, ftr |
| MPP/PE | 157, as | 258, as | 0.91, as | 1.49, as |
| MPP/PP | 276, as | 314, as, ftr | 1.60, as | 1.82, as, ftr |
| BF/3 mil PP | 360, as, zip | 611, as, zip | 2.08, as, zip | 3.54, as, zip |
| BF/N | 241, as, zip | 138, as, zip | 1.40, as, zip | 0.80, as, zip |
| N/3 mil PP | 184, as, zip | 864, as, zip | 1.07, as, zip | 5.00, as, zip |

Example 19

Polyester of Example 3 was evaluated with Isocyanate Pre-Polymer I (17.9% Isocyanate) at a mix ratio of Isocyanate Pre-Polymer I:Polyester 3 of 100:91 (molar NCO:OH, 1.52:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 240 ftr, as | 349, as | 1.39, ftr, as | 2.02, as |
| PP/PE | 665, ftr | 327, as, zip | 3.85, ftr | 1.89, as, zip |
| PET/PE | 488, as, zip | 1024, ftr | 2.83, as, zip | 5.93, ftr |
| N/PE | 330, as, zip | 445, as | 1.91, as, zip | 2.58, as |
| MPET/PE | 67, as, zip | 177, as | 0.39, as, zip | 1.03, as |
| MPP/PE | 102, as | 306, as | 0.59, as | 1.77, as |
| MPP/PP | 81, as | 225, as, zip | 0.47, as | 1.30, as, zip |
| BF/3 mil PP | 95, as | 568, as, zip | 0.55, as | 3.29, as, zip |
| BF/N | 143, as | 158, as; zip | 0.83, as | 0.92, as, zip |
| N/3 mil PP | 252, as, zip | 639, ftr, as | 1.46, as, zip | 3.70, ftr, as |

Example 20

Polyester of Example 5 was evaluated with Isocyanate Pre-Polymer I (17.9% Isocyanate) at a mix ratio of Isocyanate Pre-Polymer I:Polyester 5 of 100:93 (molar NCO:OH, 1.38:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 109, as | 359, ftr | 0.63, as | 2.08, ftr |
| PP/PE | 254, ftr | 488, ftr | 1.47, ftr | 2.83, ftr |
| PET/PE | 352, ftr | 508, ftr | 2.04, ftr | 2.94, ftr |
| N/PE | 386, ftr | 544, ftr | 2.24, ftr | 3.15, ftr |
| MPET/PE | 342, ftr | 554, ftr | 1.98, ftr | 321, ftr |
| MPP/PE | 262, ftr | 461, ftr | 1.52, ftr | 2,67, ftr |
| MPP/PP | 125, ftr | 301, ftr | 0.72, ftr | 1.74, ftr |
| BF/3 mil PP | 138, as, zip | 567, as | 0.80, as, zip | 3.28, as |
| BF/N | 74, as, zip | 236, as | 0.43, as, zip | 1.37, as |
| N/3 mil PP | 112, as, zip | 1160, ftr | 0.65, as, zip | 6.72, ftr |

Example 21

Polyester of Example 6 was evaluated with Isocyanate Pre-Polymer I (17.9% Isocyanate) at a mix ratio of Isocyanate Pre-Polymer I:Polyester 6 of 100:93 (molar NCO:OH, 1.36:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 38, as | 323, ftr | 0.22, as | 1.87, ftr |
| PP/PE | 153, as | 378, ftr | 0.89, as | 2.19, ftr |
| PET/PE | 87, as | 999, ftr | 0.50, as | 5.79, ftr |
| N/PE | 98, as, zip | 714, ftr | 0.57, as, zip | 4.14, ftr |
| MPET/PE | 100, as, zip | 409, ftr | 0.58, as, zip | 2.37, ftr |
| MPP/PE | 109, as, zip | 528, ftr | 0.63, as, zip | 3.06, ftr |
| MPP/PP | 53, as, zip | 391, ftr | 0.31, as, zip | 2.26, ftr |
| BF/3 mil PP | 103, as | 579, as, zip | 0.60, as, zip | 3.35, as, zip |
| BF/N | 43, as | 311, as, zip | 0.25, as | 1.80, as, zip |
| N/3 mil PP | 63, as, zip | 347, as, zip | 0.36, as, zip | 2.01, as, zip |

Example 22

Polyester of Example 7 was evaluated with Isocyanate Pre-Polymer I (17.9% Isocyanate) at a mix ratio of Isocyanate Pre-Polymer I:Polyester 7 of 100:104 (molar NCO:OH, 1.38:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | Bond Strength (N/15 mm) | |
|---|---|---|---|---|
| | 1 Day | 7 Day | 1 Day | 7 Day |
| PP/PP | 97, ftr | 384, ftr | 0.56, ftr | 2.22, ftr |
| PP/PE | 200, ftr | 438, ftr | 1.16, ftr | 2.54, ftr |
| PET/PE | 203, as, zip | 1145, ftr | 1.18, as, zip | 6.63, ftr |
| N/PE | 122, as, zip | 618, ftr | 0.71, as, zip | 3.58, ftr |
| MPET/PE | 249, as, zip | 622, ftr | 1.44, as, zip | 3.60, ftr |
| MPP/PE | 169, as | 828, ftr | 0.98, as | 4.80, ftr |
| MPP/PP | 124, as, zip | 454, ftr | 0.72, as, zip | 2.63, ftr |
| BF/3 mil PP | 185, as | 436, as, zip | 1.07, as | 2.53, as, zip |
| BF/N | 96, as | 323, as, zip | 0.56, as | 1.87, as, zip |
| N/3 mil PP | 192, as | 536, as, zip | 1.11, as | 3.10, as, zip |

Example 23

Polyester of Example 4 was evaluated with Isocyanate Pre-Polymer II (MDI-based polyurethane prepolymer composed of 69-71% isocyanate-terminated polyurethane resin and 29-31% of a mixture of 4,4'-MDI and 2,4'-MDI; and having 13% isocyanate groups) at a mix ratio of Isocyanate Pre-Polymer II:Polyester 4 of 100:75 (molar NCO:OH, 1.50:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | >24 Hr Water Soak | 1 Day | 7 Day | >24 Hr Water Soak |
| PP/PP | 377, ftr | 297, ftr | 186, ftr | 2.18, ftr | 1.72, ftr | 1.08, ftr |
| PP/PE | 544, ftr | 1232, ftr | 516, ftr | 3.15, ftr | 7.14, ftr | 2.99, ftr |
| PET/PE | 793, ftr | 1368, ftr | 168, ftr | 4.59, ftr | 7.92, ftr | 0.97, ftr |
| N/PE | 726, ftr | 1116, ftr | 1365, ftr | 4.20, ftr | 6.46, ftr | 7.91, ftr |
| MPET/PE | 349, ftr | 499, ftr | 33, as | 2.02, ftr | 2.89, ftr | 0.19, as |
| MPP/PE | 509, ftr | 1420, ftr | 1274, ftr | 2.95, ftr | 8.22, ftr | 7.38, ftr |
| MPP/PP | 474, ftr | 386, ftr | 381, ftr | 2.75, ftr | 2.24, ftr | 2.21, ftr |
| BF/3 mil PP | 549, as | 743, as | 387, as | 3.18, as | 4.30, as | 2.24, as |
| BF/N | 317, as | 707, as | 214, ftr | 1.84, as | 4.09, ftr | 1.24, ftr |
| N/3 mil pp | 352, as | 1540, ftr | 1050, ftr | 2.04, as | 8.92, ftr | 6.08, ftr |

Example 24

Polyester of Ex. 5 was evaluated with Isocyanate pre-polymer II (13.0% isocyanate) at a mix ratio of Isocyanate pre-polymer II:Polyester 5 of 100:65 (molar NCO:OH, 1.73:1) from a 50% ethyl acetate solution to yield a coating weight of 1.0 lbs/rm (1.6276 g/m$^2$). Bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | >24 Hr Water Soak | 1 Day | 7 Day | >24 Hr Water Soak |
| PP/PP | 680, ftr | 1506, ftr | 437, ftr | 3.94, ftr | 8.72, ftr | 2.53, ftr |
| PP/PE | 713, ftr | 1004, ftr | 405, ftr | 4.13, ftr | 5.81, ftr | 2.35, ftr |
| PET/PE | 814, ftr | 1379, ftr | 428, ftr | 4.71, ftr | 7.99, ftr | 2.48, ftr |
| N/PE | 779, ftr | 1446, ftr | 830, ftr | 4.51, ftr | 8.37, ftr | 4.81, ftr |
| MPET/PE | 564, ftr | 560, ftr | 18, as | 3.27, ftr | 3.24, ftr | 0.10, as |
| MPP/PE | 898, ftr | 1059, ftr | 442, as | 5.20, ftr | 6.13, ftr | 2.56, as |
| MPP/PP | 560, ftr | 256, ftr | 154, as | 3.24, ftr | 1.48, ftr | 0.89, as |
| BF/3 mil PP | 431, as | 771, as | 113, as | 2.50, as | 4.47, as | 0.65, as |
| BF/N | 360, as | 1143, ftr | 73, ftr | 2.08, as | 6.62, ftr | 0.42, ftr |
| N/3 mil pp | 717, ftr | 1728, ftr | 272, as | 4.15, ftr | 10.01, ftr | 1.58, as |

Example 25

Polyester of Example 6 was evaluated with Isocyanate Pre-Polymer II (13.0% Isocyanate) at a mix ratio of Isocyanate Pre-Polymer II:Polyester 6 of 100:65 (molar NCO:OH, 1.41:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 273. ftr | 440, ftr | 485, ftr | 1.58, ftr | 2.55, ftr | 2.81, ftr |
| PP/PE | 238, ftr | 587, ftr | 680, ftr | 1.38, ftr | 3.40, ftr | 3.94, ftr |
| PET/PE | 350, ftr | 969, ftr | 197, as | 2.03, ftr | 5.61, ftr | 1.14, as |
| N/PE | 291, as, zip | 1384, ftr | 630, ftr | 1.69, as, zip | 8.02, ftr | 3.65, ftr |
| MPET/PE | 272, ftr | 990, ftr | 28, as | 1.58, ftr | 5.73, ftr | 0.16, as |
| MPP/PE | 291, ftr | 1434, ftr | 1249, ftr | 1.69, ftr | 8.31, ftr | 7.23, ftr |
| MPP/PP | 276, as | 790, ftr | 363, ftr | 1.60, as | 4.58, ftr | 2.10, ftr |
| BF/3 mil PP | 138, as | 810, as | 340, as | 0.80, as | 4.69, as | 1.97, as |
| BF/N | 118, as, zip | 850, ftr | 103, as | 0.68, as, zip | 4.92, ftr | 0.60, as |
| N/3 mil PP | 150, as. zip | 1794, ftr | 313, ftr | 0.87, as, zip | 10.39, ftr | 1.81, ftr |

Pot-Life Stability for the polyester of Example 6 was evaluated with Isocyanate Pre-Polymer II (13.0% Isocyanate) at a mix ratio of Isocyanate Pre-Polymer II:Polyester 6 of 100:70 (molar NCO:OH, 1.41:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1225 | 20.0 | 32.0 | 3737.5 |
| 50 | 762.5 | 15.5 | 31.0 | 3825.0 |

Example 26

Polyester of Example 6 was evaluated with Isocyanate Pre-Polymer II (13.0% Isocyanate) at a mix ratio of Isocyanate Pre-Polymer II:Polyester 6 of 100:70 (molar NCO:OH, 1.31:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 193, ftr | 246, ftr | 309, ftr | 1.12, ftr | 1.42, ftr | 1.79, ftr |
| PP/PE | 352, ftr | 575, ftr | 548, ftr | 2.04, ftr | 3.33, ftr | 3.17, ftr |
| PET/PE | 422, ftr | 699, ftr | 50, as | 2.44, ftr | 405, ftr | 0.29, as |
| N/PE | 330, ftr | 656, ftr | 185, ftr | 1.91, ftr | 3.80, ftr | 1.07, ftr |
| MPET/PE | 260, ftr | 366, ftr | 9, as | 1.51, ftr | 2.12, ftr | 0.05, as |
| MPP/PE | 272, ftr | 667, ftr | 515, ftr | 1.58, ftr | 3.86, ftr | 2.98, ftr |
| MPP/PP | 186, ftr | 428, ftr | 299, ftr | 1.08, ftr | 2.48, ftr | 1.73, ftr |
| BF/3 mil PP | 85, as | 314, as | 161, as | 0.49, as | 1.82, as | 0.93, as |
| BF/N | 24, as | 258, ftr | 57, as | 0.14, as | 1.49, ftr | 0.33, as |
| N/3 mil PP | 72, as | 824, ftr | 43, as | 0.42, as | 4.77, ftr | 0.25, as |

Example 27

Polyester of Example 7 was evaluated with Isocyanate Pre-Polymer II (13.0% Isocyanate) at a mix ratio of Isocyanate Pre-Polymer II:Polyester 7 of 100:73 (molar NCO:OH, 1.60:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 284, ftr | 989, ftr | 280, ftr | 1.64, ftr | 5.73, ftr | 1.62, ftr |
| PP/PE | 1007, ftr | 1267, ftr | 343, ftr | 5.83, ftr | 7.34, ftr | 1.99, ftr |
| PET/PE | 724, ftr | 1336, ftr | 872, ftr | 4.19, ftr | 7.74, ftr | 5.05, ftr |
| N/PE | 508, as, zip | 1360, ftr | 841, ftr | 2.94, as, zip | 7.88, ftr | 4.87, ftr |
| MPET/PE | 234, ftr | 1195, ftr | 37, as | 1.36, ftr | 6.92, ftr | 0.21, as |
| MPP/PE | 386, ftr | 1066, ftr | 1171, ftr | 2.24, ftr | 6.17, ftr | 6.78, ftr |
| MPP/PP | 86, as, zip | 617, ftr | 406, ftr | 0.50, as, zip | 3.57, ftr | 2.35, ftr |
| BF/3 mil PP | 35, as | 853, as | 351, as | 0.20, as | 4.94, as | 2.03, as |
| BF/N | 269, as, zip | 496, as | 36, as | 1.56, as, zip | 2.87, as | 0.21, as |
| N/3 mil pp | 252, as, zip | 1358, ftr | 56, as | 1.46, as, zip | 7.86, ftr | 0.32, as |

Pot-Life Stability of the polyester of Example 7 was evaluated with Isocyanate Pre-Polymer II (13.0% Isocyanate) at a mix ratio of Isocyanate Pre-Polymer II:Polyester 7 of 100:73 (molar NCO:OH, 1.60:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1612.5 | 21.75 | 26.5 | 4637.5 |
| 50 | 925.0 | 14.5 | 25.0 | 5462.5 |

Example 28

Polyester of Example 8 was evaluated with Isocyanate Pre-Polymer II (13.0% Isocyanate) at a mix ratio of Isocyanate Pre-Polymer II:Polyester 8 of 100:65 (molar NCO:OH, 1.43:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 313, ftr | 206, ftr | 219, ftr | 1.81, ftr | 1.19, ftr | 1.27, ftr |
| PP/PE | 207, ftr | 252, ftr | 4, as | 1.20, ftr | 1.46, ftr | 0.02, as |
| PET/PE | 550, ftr | 1417, ftr | 1388, ftr | 3.19, ftr | 8.21, ftr | 8.04, ftr |
| N/PE | 758, ftr | 824, ftr | 299, ftr | 4.39, ftr | 4.77, ftr | 1.73, ftr |
| MPET/PE | 488, ftr | 901, ftr | 476, ftr | 2.83, ftr | 5.22, ftr | 2.76, ftr |
| MPP/PE | 912, ftr | 1021, ftr | 1475, ftr | 5.28, ftr | 5.91, ftr | 8.54, ftr |
| MPP/PP | 329, ftr | 373, ftr | 1338, ftr | 1.91, ftr | 2.16, ftr | 7.75, ftr |
| BF/3 mil PP | 663, as | 771, as | 231, as | 3.84, as | 4.47, as | 1.34, as |
| BF/N | 433, ftr | 361, as | 45, as | 2.51, ftr | 2.09, ftr | 0.26, as |
| N/3 mil PP | 463, ftr | 837, ftr | 253, ftr | 2.68, ftr | 4.85, ftr | 1.47, ftr |

Pot-Life Stability of the polyester of Example 8 was evaluated with Isocyanate Pre-Polymer II (13.0% Isocyanate) at a mix ratio of Isocyanate Pre-Polymer II:Polyester 8 of 100:65 (molar NCO:OH, 1.43:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1800 | 20.25 | 22.5 | 5587.5 |
| 50 | 1112.5 | 15.0 | 23.25 | 6137.5 |

Example 29

Polyester of Example 9 was evaluated with Isocyanate Pre-Polymer II (13.0% Isocyanate) at a mix ratio of Isocyanate Pre-Polymer II:Polyester 9 of 100:65 (molar NCO:OH, 1.44:1) from a 50% Ethyl Acetate solution to yield a coating weight of 1.0 lbs/rm (1.6276 g/m²). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 381, ftr | 364, ftr | 123, as | 2.21, ftr | 2.11, ftr | 0.71, as |
| PP/PE | 405, ftr | 604, ftr | 82, ftr | 2.35, ftr | 3.50, ftr | 0.47, ftr |
| PET/PE | 734, ftr | 304, ftr | 130, ftr | 4.25, ftr | 1.76, ftr | 0.75, ftr |
| N/PE | 680, ftr | 1143, ftr | 105, ftr | 3.94, ftr | 6.62, ftr | 0.61, ftr |
| MPET/PE | 548, ftr | 337, ftr | 50, ftr | 3.17, ftr | 1.95, ftr | 0.29, ftr |
| MPP/PE | 353, ftr | 409, ftr | 719, ftr | 2.04, ftr | 2.37, ftr | 4.16, ftr |
| MPP/PP | 372, ftr | 442, ftr | 244, ftr | 2.15, ftr | 2.56, ftr | 1.41, ftr |
| BF/3 mil PP | 357, as | 161, as | 177, as | 2.07, as | 0.93, as | 1.03, as |
| BF/N | 390, ftr | 358, ftr | 79, as | 2.26, ftr | 2.07, ftr | 0.46, as |
| N/3 mil PP | 642, ftr | 1281, ftr | 56, as | 3.72, ftr | 7.42, ftr | 0.32, as |

Pot-Life Stability of the polyester of Example 9 was evaluated with Isocyanate Pre-Polymer II (13.0% Isocyanate) at a mix ratio of Isocyanate Pre-Polymer II:Polyester 9 of 100:65 (molar NCO:OH, 1.44:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 2137.5 | 18.75 | 17.5 | 7512.5 |
| 50 | 1200.0 | 13.25 | 19.25 | 8825.0 |

Example 30

Polyester of Example 10 was evaluated with Isocyanate Pre-Polymer II (13.0% Isocyanate) at a mix ratio of Isocyanate Pre-Polymer II:Polyester 10 of 100:65 (molar NCO:OH, 1.48:1) from a 50% Ethyl Acetate solution to yield a coating weight of 1.0 lbs/rm (1.6276 g/m²). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 270, ftr | 305, ftr | 212, ftr | 1.56, ftr | 1.77, ftr | 1.23, ftr |
| PP/PE | 330, ftr | 750, ftr | 561, ftr | 1.91, ftr | 4.34, ftr | 3.25, ftr |
| PET/PE | 675, ftr | 736, ftr | 186, ftr | 3.91, ftr | 4.26, ftr | 1.08, ftr |
| N/PE | 614, ftr | 589, ftr | 134, as | 3.56, ftr | 3.41, ftr | 0.78, as |
| MPET/PE | 645, ftr | 724, ftr | 25, as | 3.74, ftr | 4.19, ftr | 0.15, as |
| MPP/PE | 540, ftr | 534, ftr | 346, ftr | 3.13, ftr | 3.09, ftr | 2.00, ftr |
| MPP/PP | 267, ftr | 294, ftr | 250, ftr | 1.55, ftr | 1.70, ftr | 1.45, ftr |
| BF/3 mil PP | 213, as | 227, as | 36, as | 1.23, as | 1.31, as | 0.21, as |
| BF/N | 196, as | 206, as | 29, as | 1.14, as | 1.19, as | 0.17, as |
| N/3 mil PP | 332, ftr | 823, ftr | 50, as | 1.93, ftr | 4.77, ftr | 0.29, as |

Pot-Life Stability of the polyester of Example 10 was evaluated with Isocyanate Pre-Polymer II (13.0% Isocyanate) at a mix ratio of Isocyanate Pre-Polymer II:Polyester 10 of 100:65 (molar NCO:OH, 1.48:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1700.0 | 20.25 | 24.0 | 5225.0 |
| 50 | 1025.0 | 15.25 | 25.25 | 5287.5 |

Example 31

Polyester of Example 10 was evaluated with Isocyanate Pre-Polymer II (13.0% Isocyanate) at a mix ratio of Isocyanate Pre-Polymer II:Polyester 10 of 100:75 (molar NCO:OH, 1.28:1) from a 50% Ethyl Acetate solution to yield a coating weight of 1.0 lbs/rm (1.6276 g/m²). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 458, ftr | 340, ftr | 296, ftr | 2.65, ftr | 1.97, ftr | 1.71, ftr |
| PP/PE | 318, ftr | 311, ftr | 394, ftr | 1.84, ftr | 1.80, ftr | 2.28, ftr |
| PET/PE | 670, ftr | 621, ftr | 282, ftr | 3.88, ftr | 3.60, ftr | 1.63, ftr |
| N/PE | 508, ftr | 823, ftr | 14, as | 2.94, ftr | 4.77, ftr | 0.08, as |
| MPET/PE | 471, ftr | 438, ftr | 58, as | 2.73, ftr | 2.54, ftr | 0.34, as |
| MPP/PE | 552, ftr | 579, ftr | 520, ftr | 3.20, ftr | 3.35, ftr | 3.01, ftr |
| MPP/PP | 299, ftr | 328, ftr | 505, ftr | 1.73, ftr | 1.90, ftr | 2.92, ftr |
| BF/3 mil PP | 169, as | 210, as | 114, as | 0.98, as | 1.22, as | 0.66, as |
| BF/N | 186, as | 242, ftr | 36, as | 1.08, as | 1.40, ftr | 0.21, as |
| N/3 mil PP | 294, ftr | 1253, ftr | 85, as | 1.70, ftr | 7.26, ftr | 0.49, as |

Example 32

Polyester of Example 11 was evaluated with Isocyanate Pre-Polymer II (13.0% Isocyanate) at a mix ratio of Isocyanate Pre-Polymer II:Polyester 11 of 100:65 (molar NCO:OH, 1.47:1) from a 50% Ethyl Acetate solution to yield a coating weight of 1.0 lbs/rm (1.6276 g/m²). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 381, ftr | 502, ftr | 351, ftr | 2.21, ftr | 2.91, ftr | 2.03, ftr |
| PP/PE | 285, ftr | 864, ftr | 531, ftr | 1.65, ftr | 5.00, ftr | 3.08, ftr |
| PET/PE | 580, ftr | 660, ftr | 205, ftr | 3.36, ftr | 3.82, ftr | 1.19, ftr |
| N/PE | 685, ftr | 563, ftr | 18, as | 3.97, ftr | 3.26, ftr | 0.10, as |
| MPET/PE | 566, ftr | 719, ftr | 257, ftr | 3.28, ftr | 4.16, ftr | 1.49, ftr |
| MPP/PE | 495, ftr | 886, ftr | 689, ftr | 2.87, ftr | 5.13, ftr | 3.99, ftr |
| MPP/PP | 370, ftr | 494, ftr | 462, ftr | 2.14, ftr | 2.86, ftr | 2.68, ftr |
| BF/3 mil PP | 242, as | 481, as | 114, as | 1.40, as | 2.79, as | 0.66, as |
| BF/N | 165, as | 182, as | 40, as | 0.96, as | 1.05, as | 0.23, as |
| N/3 mil PP | 175, as | 850, ftr | 11, as | 1.01, as | 4.92, ftr | 0.06, as |

Pot-Life Stability of the polyester of Example 11 was evaluated with Isocyanate Pre-Polymer II (13.0% Isocyanate) at a mix ratio of Isocyanate Pre-Polymer II:Polyester 11 of 100:65 (molar NCO:OH, 1.47:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1800 | 19.5 | 21.5 | 6012.5 |
| 50 | 1012.5 | 13.0 | 21.75 | 7037.5 |

Example 33

Polyester of Example 11 was evaluated with Isocyanate Pre-Polymer II (13.0% Isocyanate) at a mix ratio of Isocyanate Pre-Polymer II:Polyester 11 of 100:70 (molar NCO:OH, 1.36:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 356, ftr | 277, ftr | 397, ftr | 2.06, ftr | 1.60, ftr | 2.30, ftr |
| PP/PE | 293, ftr | 470, ftr | 471, ftr | 1.70, ftr | 2.72, ftr | 2.73, ftr |
| PET/PE | 705, ftr | 669, ftr | 242, ftr | 4.08, ftr | 3.87, ftr | 1.40, ftr |
| N/PE | 589, ftr | 610, ftr | 21, as | 3.41, ftr | 3.53, ftr | 0.12, as |
| MPET/PE | 550, ftr | 567, ftr | 160, ftr | 3.19, ftr | 3.28, ftr | 0.93, ftr |
| MPP/PE | 332, ftr | 874, ftr | 584, ftr | 1.92, ftr | 5.06, ftr | 3.38, ftr |
| MPP/PP | 225, ftr | 429, ftr | 421, ftr | 1.30, ftr | 2.48, ftr | 2.44, ftr |
| BF/3 mil PP | 88, as | 198, as | 40, as | 0.51, as | 1.15, as | 0.23, as |
| BF/N | 226, ftr | 229, ftr | 43, as | 1.31, ftr | 1.33, ftr | 0.25, as |
| N/3 mil PP | 377, ftr | 927, ftr | 15, as | 2.18, ftr | 5.37, ftr | 0.09, as |

Example 34

Polyester of Example 12 was evaluated with Isocyanate Pre-Polymer II (13.0% Isocyanate) at a mix ratio of Isocyanate Pre-Polymer II:Polyester 12 of 100:75 (molar NCO:OH, 1.44:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 130, ftr | 309, ftr | 454, ftr | 0.75, ftr | 1.79, ftr | 2.63, ftr |
| PP/PE | 259, ftr | 559, ftr | 459, ftr | 1.50, ftr | 3.24, ftr | 2.66, ftr |
| PET/PE | 270, ftr | 612, ftr | 522, ftr | 1.56, ftr | 3.54, ftr | 3.02, ftr |
| N/PE | 238, ftr | 788, ftr | 419, ftr | 1.38, ftr | 4.56, ftr | 2.43, ftr |
| MPET/PE | 203, ftr | 500, ftr | 301, ftr | 1.18, ftr | 2.90, ftr | 1.74, ftr |
| MPP/PE | 248, ftr | 1050, ftr | 767, ftr | 1.44, ftr | 6.08, ftr | 4.44, ftr |
| MPP/PP | 103, ftr | 314, ftr | 268, ftr | 0.60, ftr | 1.82, ftr | 1.55, ftr |
| BF/3 mil PP | 98, as | 355, as | 112, as | 0.57, as | 2.06, as | 0.65, as |
| BF/N | 104, as | 290, as | 35, as | 0.60, as | 1.68, as | 0.20, as |
| N/3 mil PP | 130, as | 735, ftr | 19, as | 0.75, as | 4.26, ftr | 0.11, as |

Pot-Life Stability of the polyester of Example 12 was evaluated with Isocyanate Pre-Polymer II (13.0% Isocyanate) at a mix ratio of Isocyanate Pre-Polymer II:Polyester 12 of 100:75 (molar NCO:OH, 1.44:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1100.0 | 14.0 | 23.5 | 5650.0 |
| 50 | 612.5 | 10.5 | 24.25 | 6725.0 |

Example 35

Polyester of Example 12 was evaluated with Isocyanate Pre-Polymer II (13.0% Isocyanate) at a mix ratio of Isocyanate Pre-Polymer II Polyester 12 of 100:70 (molar NCO:OH, 1.54:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 138, ftr | 372, ftr | 416, ftr | 0.80, ftr | 2.15, ftr | 2.41, ftr |
| PP/PE | 251, ftr | 607, ftr | 453, ftr | 1.45, ftr | 3.52, ftr | 2.62, ftr |
| PET/PE | 445, ftr | 684, ftr | 180, as | 2.58, ftr | 3.96, ftr | 1.04, ftr |
| N/PE | 259, ftr | 564, ftr | 468, ftr | 1.50, ftr | 3.27, ftr | 2.71, ftr |
| MPET/PE | 302, ftr | 860, ftr | 33, as | 1.75, ftr | 4.98, ftr | 0.19, as |
| MPP/PE | 294, ftr | 567, ftr | 577, ftr | 1.70, ftr | 3.28, ftr | 3.34, ftr |
| MPP/PP | 112, ftr | 405, ftr | 419, ftr | 0.65, ftr | 2.35, ftr | 2.43, ftr |
| BF/3 mil PP | 98, as | 396, as | 180, as | 0.57, as | 2.29, as | 1.04, as |
| BF/N | 96, as | 198, as | 26, as | 0.56, as | 1.15, as | 0.15, as |
| N/3 mil PP | 82, as | 861, ftr | 85, as | 0.47, as | 4.99, ftr | 0.49, as |

Example 36

Polyester of Example 13 was evaluated with Isocyanate Pre-Polymer II (13.0% Isocyanate) at a mix ratio of Isocyanate Pre-Polymer II:Polyester 13 of 100:65 (molar NCO:OH, 1.48:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 448, ftr | 357, ftr | 291, ftr | 2.59, ftr | 2.07, ftr | 1.69, ftr |
| PP/PE | 418, ftr | 581, ftr | 363, ftr | 2.42, ftr | 3.36, ftr | 2.10, ftr |
| PET/PE | 777, ftr | 1018, ftr | 162, as | 4.50, ftr | 5.90, ftr | 0.94, as |
| N/PE | 679, ftr | 812, ftr | 58, as | 3.93, ftr | 4.70, ftr | 0.34, as |
| MPET/PE | 478, ftr | 806, ftr | 42, as | 2.77, ftr | 4.67, ftr | 0.24, as |
| MPP/PE | 456, ftr | 1198, ftr | 607, ftr | 2.64, ftr | 6.94, ftr | 1.08, ftr |
| MPP/PP | 362, ftr | 432, ftr | 440, ftr | 2.10, ftr | 2.50, ftr | 0.39, ftr |
| BF/3 mil PP | 50, as | 21, as | 30, as | 0.29, as | 0.12, as | 0.17, as |
| BF/N | 142, as | 278, ftr | 52, as | 0.82, as | 1.61, ftr | 0.30, as |
| N/3 mil PP | 37, as | 526, ftr | 10, as | 0.21, as | 3.05, ftr | 0.06, as |

Pot-Life Stability for the polyester of Example 13 was evaluated with Isocyanate Pre-Polymer II (13.0% Isocyanate) at a mix ratio of Isocyanate Pre-Polymer II:Polyester 13 of 100:65 (molar NCO:OH, 1.48:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 1237.5 | 19.25 | 29.5 | 4100 |
| 50 | 737.5 | 13.75 | 28.25 | 4462.5 |

Example 37

Polyester of Example 13 was evaluated with Isocyanate Pre-Polymer II (13.0% Isocyanate) at a mix ratio of Isocyanate Pre-Polymer II:Polyester 13 of 100:70 (molar NCO:OH, 1.37:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 230, ftr | 460, ftr | 461, ftr | 1.33, ftr | 2.66, ftr | 2.67, ftr |
| PP/PE | 514, ftr | 992, ftr | 614, ftr | 2.98, ftr | 5.75, ftr | 3.56, ftr |
| PET/PE | 618, ftr | 907, ftr | 620, ftr | 3.58, ftr | 5.25, ftr | 3.59, ftr |
| N/PE | 408, ftr | 726, ftr | 134, ftr | 2.36, ftr | 4.20, ftr | 0.78, ftr |
| MPET/PE | 414, ftr | 1287, ftr | 372, ftr | 2.40, ftr | 7.45, ftr | 2.15, ftr |
| MPP/PE | 403, ftr | 870, ftr | 566, ftr | 2.33, ftr | 5.04, ftr | 3.28, ftr |
| MPP/PP | 189, ftr | 490, ftr | 404, ftr | 1.09, ftr | 2.84, ftr | 2.34, ftr |
| BF/3 mil PP | 51, as | 165, as | 52, as | 0.30, as | 0.96, as | 0.30, as |
| BF/N | 103, as | 271, ftr | 41, as | 0.60, as | 1.57, ftr | 0.24, as |
| N/3 mil PP | 57, as | 553, ftr | 21, as | 0.33, as | 3.20, ftr | 0.12, as |

Example 38

Polyester of Example 14 was evaluated with Isocyanate Pre-Polymer II (13.0% Isocyanate) at a mix ratio of Isocyanate Pre-Polymer II:Polyester 14 of 100:65 (molar NCO:OH, 1.41:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 145, ftr | 289, ftr | 274, ftr | 0.84, ftr | 1.67, ftr | 1.59, ftr |
| PP/PE | 237, ftr | 623, ftr | 286, ftr | 1.37, ftr | 3.61, ftr | 1.66, ftr |
| PET/PE | 391, ftr | 1080, ftr | 536, ftr | 2.26, ftr | 6.25, ftr | 3.10, ftr |
| N/PE | 367, ftr | 950, ftr | 95, ftr | 2.13, ftr | 5.50, ftr | 0.55, ftr |
| MPET/PE | 330, ftr | 736, ftr | 71, ftr | 1.91, ftr | 4.26, ftr | 0.41, ftr |
| MPP/PE | 272, ftr | 764, ftr | 634, ftr | 1.58, ftr | 4.42, ftr | 3.67, ftr |
| MPP/PP | 124, as | 337, ftr | 320, ftr | 0.72, as | 1.95, ftr | 1.85, ftr |
| BF/3 mil PP | 78, as | 87, as | 121, ftr | 0.45, as | 0.50, as | 0.70, ftr |
| BF/N | 89, as | 308, ftr | 0 | 0.52, as | 1.78, ftr | 0 |
| N/3 mil PP | 62, as | 188, ftr | 30, as | 0.36, as | 1.09, ftr | 0.17, as |

Pot-Life Stability was examined for Polyester of Example 14 was evaluated with Isocyanate Pre-Polymer II (13.0% Isocyanate) at a mix ratio of Isocyanate Pre-Polymer II:Polyester 14 of 100:65 (molar NCO:OH, 1.41:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
|---|---|---|---|---|
| 40 | 962.5 | 18.5 | 35.3 | 3250.0 |
| 50 | 625.0 | 14.5 | 34.3 | 3262.5 |

Example 39

Polyester of Example 14 was evaluated with Isocyanate Pre-Polymer II (13.0% Isocyanate) at a mix ratio of Isocyanate Pre-Polymer II:Polyester 14 of 100:70 (molar NCO:OH, 1.31:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
|---|---|---|---|---|---|---|
| Laminate Structure | 1 Day | 7 Day | After 24 Hr Water Soak | 1 Day | 7 Day | After 24 Hr Water Soak |
| PP/PP | 191, ftr | 189, ftr | 519, ftr | 1.11, ftr | 1.09, ftr | 3.01, ftr |
| PP/PE | 246, ftr | 498, ftr | 615, ftr | 1.42, ftr | 2.88, ftr | 3.56, ftr |
| PET/PE | 390, ftr | 835, ftr | 371, ftr | 2.26, ftr | 4.84, ftr | 2.15, ftr |
| N/PE | 233, ftr | 941, ftr | 76, ftr | 1.35, ftr | 5.45, ftr | 0.44, ftr |
| MPET/PE | 248, ftr | 593, ftr | 260, ftr | 1.44, ftr | 3.43, ftr | 1.51, ftr |
| MPP/PE | 279, ftr | 429, ftr | 684, ftr | 1.62, ftr | 2.48, ftr | 3.96, ftr |
| MPP/PP | 123, as | 450, ftr | 289, ftr | 0.71, ftr | 2.61, ftr | 1.67, ftr |
| BF/3 mil PP | 89, as | 165, as | 0 | 0.52, as | 0.96, as | 0 |
| BF/N | 43, as | 354, ftr | 32, ftr | 0.25, as | 2.05, ftr | 0.19, ftr |
| N/3 mil PP | 78, as | 460, ftr | 0 | 0.45, as | 2.66, ftr | 0 |

Example 40

Polyester of Example 15 was evaluated with Isocyanate Pre-Polymer II (13.0% Isocyanate) at a mix ratio of Isocyanate Pre-Polymer II:Polyester 15 of 100:70 (molar NCO:OH, 1.45:1) from a 50% Ethyl Acetate solution to yield a coating weight of 1.0 lbs/rm (1.6276 g/m$^2$). The bond strength was examined as a function of curing time and is reported below.

|  | Bond Strength (g/lin) | | | Bond Strength (N/15 mm) | | |
| --- | --- | --- | --- | --- | --- | --- |
| Laminate Structure | 1 Day | 7 Day | After 24 Hr Water Soak | 1 Day | 7 Day | After 24 Hr Water Soak |
| PP/PP | 196, ftr | 362, ftr | 519, ftr | 1.14, ftr | 2.10, ftr | 3.01, ftr |
| PP/PE | 268, ftr | 415, ftr | 441, ftr | 1.55, ftr | 2.40, ftr | 2.55, ftr |
| PET/PE | 472, ftr | 837, ftr | 304, ftr | 2.73, ftr | 4.85, ftr | 1.76, ftr |
| N/PE | 267, ftr | 623, ftr | 393, ftr | 1.55, ftr | 3.61, ftr | 2.28, ftr |
| MPET/PE | 374, ftr | 405, ftr | 35, as | 2.17, ftr | 2.35, ftr | 0.20, as |
| MPP/PE | 266, ftr | 567, ftr | 465, ftr | 1.54, ftr | 3.28, ftr | 1.85, ftr |
| MPP/PP | 113, ftr | 426, ftr | 349, ftr | 0.65, ftr | 2.47, ftr | 1.02, ftr |
| BF/3 mil PP | 102, ftr | 533, as | 17, as | 0.59, ftr | 3.09, as | 0.10, as |
| BF/N | 98, as | 348, ftr | 12, as | 0.57, as | 2.02, ftr | 0.07, as |
| N/3 mil PP | 70, as | 385, ftr | 10, as | 0.41, as | 2.23, ftr | 0.06, as |

Pot-Life Stability of the polyester of Example 15 was evaluated with Isocyanate Pre-Polymer II (13.0% Isocyanate) at a mix ratio of Isocyanate Pre-Polymer II Polyester 15 of 100:70 (molar NCO:OH, 1.45:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
| --- | --- | --- | --- | --- |
| 40 | 1162.5 | 19.5 | 32.75 | 3600.0 |
| 50 | 737.5 | 15.3 | 32.8 | 3525.0 |

Example 41

Polyester of Ex. 15 was evaluated with Isocyanate Pre-Polymer II (13.0% Isocyanate) at a mix ratio of Isocyanate Pre-Polymer II:Polyester 15 of 100:75 (molar NCO:OH, 1.35:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
| --- | --- | --- | --- | --- | --- | --- |
| Laminate Structure | 1 Day | 7 Day | >24 Hr Water Soak | 1 Day | 7 Day | >24 Hr Water Soak |
| PP/PP | 214, ftr | 459, ftr | 454, ftr | 1.24, ftr | 2.66, ftr | 2.63, ftr |
| PP/PE | 228, ftr | 569, ftr | 293, ftr | 1.32, ftr | 3.30, ftr | 1.70, ftr |
| PET/PE | 435, ftr | 832, ftr | 479, ftr | 2.52, ftr | 4.82, ftr | 2.77, ftr |
| N/PE | 293, ftr | 369, ftr | 10, as | 1.70, ftr | 2.14, ftr | 0.06, as |
| MPET/PE | 257, ftr | 525, ftr | 74, as | 1.49, ftr | 3.04, ftr | 0.43, as |
| MPP/PE | 226, ftr | 907, ftr | 574, ftr | 1.31, ftr | 5.25, ftr | 3.32, ftr |
| MPP/PP | 198, ftr | 226, ftr | 375, ftr | 1.15, ftr | 1.31, ftr | 2.17, ftr |
| BF/3 mil PP | 31, as | 67, as | 0 | 0.18, as | 0.39, as | 0 |
| BF/N | 22, as | 190, ftr | 33, as | 0.13, as | 1.10, ftr | 0.19, as |
| N/3 mil PP | 10, as | 447, ftr | 20, as | 0.06, as | 2.59, ftr | 0.12, as |

Example 42

Polyester of Ex. 16 was evaluated with Isocyanate Pre-Polymer II (13.0% Isocyanate) at a mix ratio of Isocyanate Pre-Polymer II:Polyester 16 of 100:65 (molar NCO:OH, 1.54:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
| --- | --- | --- | --- | --- | --- | --- |
| Laminate Structure | 1 Day | 7 Day | >24 Hr Water Soak | 1 Day | 7 Day | >24 Hr Water Soak |
| PP/PP | 179, ftr | 228, ftr | 244, ftr | 1.04, ftr | 1.32, ftr | 1.41, ftr |
| PP/PE | 203, ftr | 495, ftr | 435, ftr | 1.18, ftr | 2.87, ftr | 2.52, ftr |
| PET/PE | 404, ftr | 922, ftr | 560, ftr | 2.34, ftr | 5.34, ftr | 3.24, ftr |
| N/PE | 297, ftr | 600, ftr | 140, ftr | 1.72, ftr | 3.47, ftr | 0.81, ftr |
| MPET/PE | 135, ftr | 194, ftr | 121, ftr | 0.78, ftr | 1.12, ftr | 0.70, ftr |
| MPP/PE | 218, ftr | 541, ftr | 650, ftr | 1.26, ftr | 3.13, ftr | 3.76, ftr |
| MPP/PP | 107, ftr | 308, ftr | 363, ftr | 0.62, ftr | 1.78, ftr | 2.10, ftr |
| BF/3 mil PP | 60, as | 81, as | 0 | 0.35, as | 0.47, as | 0 |
| BF/N | 56, as | 240, ftr | 10, as | 0.32, as | 1.39, ftr | 0.06, as |
| N/3 mil PP | 40, as | 172, ftr | 0 | 0.23, as | 1.00, ftr | 0 |

Example 43

Polyester of Example 16 was evaluated with Isocyanate Pre-Polymer II (13.0% Isocyanate) at a mix ratio of Isocyanate Pre-Polymer II:Polyester 16 of 100:70 (molar NCO:OH, 1.43:1) from a 50% Ethyl Acetate solution to yield a coating weight of 1.0 lbs/rm (1.6276 g/m²). The bond strength was examined as a function of curing time and is reported below.

|  | Bond Strength (g/lin) | | | Bond Strength (N/15 mm) | | |
| --- | --- | --- | --- | --- | --- | --- |
| Laminate Structure | 1 Day | 7 Day | After 24 Hr Water Soak | 1 Day | 7 Day | After 24 Hr Water Soak |
| PP/PP | 217, ftr | 397, ftr | 461, ftr | 1.26, ftr | 2.30, ftr | 2.67, ftr |
| PP/PE | 278, ftr | 621, ftr | 306, ftr | 1.61, ftr | 3.60, ftr | 1.77, ftr |
| PET/PE | 480, ftr | 748, ftr | 193, as | 2.78, ftr | 4.33, ftr | 1.12, as |
| N/PE | 245, ftr | 664, ftr | 45, as | 1.42, ftr | 3.85, ftr | 0.26, as |
| MPET/PE | 225, ftr | 222, ftr | 0 | 1.30, ftr | 1.29, ftr | 0 |
| MPP/PE | 184, ftr | 546, ftr | 676, ftr | 1.07, ftr | 3.16, ftr | 3.92, ftr |
| MPP/PP | 279, ftr | 798, ftr | 790, ftr | 1.62, ftr | 4.62, ftr | 4.58, ftr |
| BF/3 mil PP | 42, as | 88, as | 0 | 0.24, as | 0.51, as | 0 |
| BF/N | 83, as | 234, ftr | 88, as | 0.48, as | 1.36, ftr | 0.51, as |
| N/3 mil PP | 90, as | 171, ftr | 85, as | 0.52, as | 0.99, ftr | 0.49, as |

Pot-Life Stability of the polyester of Example 16 was evaluated with Isocyanate Pre-Polymer II (13.0% Isocyanate) at a mix ratio of Isocyanate Pre-Polymer II:Polyester 16 of 100:70 (molar NCO:OH, 143:1) at 40 and 50° C. and is reported in the following table.

| Temp (° C.) | Initial Viscosity (cps) | Time for Viscosity of 2X Initial (mins.) | Time for Viscosity of 4000 cps (mins.) | Viscosity at 30 mins. (cps) |
| --- | --- | --- | --- | --- |
| 40 | 1625.5 | 19.25 | 29.5 | 4112.5 |
| 50 | 737.5 | 14.50 | 30.5 | 3900.0 |

Example 44

Polyester of Example 16 was evaluated with Isocyanate Pre-Polymer II (13.0% Isocyanate) at a mix ratio of Isocyanate Pre-Polymer II:Polyester 16 of 100:75 (molar NCO:OH, 1.33:1) from a 50% Ethyl Acetate solution to yield a coating weight of 1.0 lbs/rm (1.6276 g/m$^2$). The bond strength was examined as a function of curing time and is reported below.

| Laminate Structure | Bond Strength (g/lin) | | | Bond Strength (N/15 mm) | | |
|---|---|---|---|---|---|---|
| | 1 Day | 7 Day | After 24 Hr Water Soak | 1 Day | 7 Day | After 24 Hr Water Soak |
| PP/PP | 234, ftr | 280, ftr | 445, ftr | 1.36, ftr | 1.62, ftr | 2.64, ftr |
| PP/PE | 261, ftr | 747, ftr | 681, ftr | 1.51, ftr | 4.33, ftr | 3.94, ftr |
| PET/PE | 334, ftr | 699, ftr | 344, ftr | 1.93, ftr | 4.05, ftr | 1.99, ftr |
| N/PE | 302, ftr | 1004, ftr | 511, ftr | 1.75, ftr | 5.81, ftr | 2.96, ftr |
| MPET/PE | 225, ftr | 222, ftr | 0 | 1.30, ftr | 1.29, ftr | 0 |
| MPP/PE | 148, ftr | 670, ftr | 418, ftr | 0.86, ftr | 3.88, ftr | 2.42, ftr |
| MPP/PP | 52, as | 357, ftr | 321, ftr | 0.30, as | 2.07, ftr | 1.86, ftr |
| BF/3 mil PP | 46, as | 77, ftr | 121, as | 0.27, as | 0.45, as | 0.70, as |
| BF/N | 56, as | 180, ftr | 21, as | 0.32, as | 1.04, ftr | 0.12, as |
| N/3 mil PP | 27, as | 320, ftr | 63, as | 0.16, as | 1.85, ftr | 0.36, as |

Example 45

Polyester of Example 6 was evaluated with Isocyanate Pre-Polymer II (13.0% Isocyanate) at a mix ratio of Isocyanate Pre-Polymer II:Polyester 6 of 100:65 (molar NCO:OH, 1.41:1) as a solventless system on a PolyType Coater at an application temperature of 40° C. to yield a coating weight indicated in table. The bond strength was examined as a function of curing time and is reported below.

| Laminate Structure | Coating Wt lbs/rm (g/m$^2$) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 1.13 (1.84) | 415, ftr | 933, ftr | 309, ftr | 2.40, ftr | 5.40, ftr | 1.79, ftr |
| PP/PE | 1.13 (1.84) | 716, ftr | 1305, ftr | 1459, ftr | 4.15, ftr | 7.56, ftr | 8.45, ftr |
| PP/PP | 1.13 (1.84) | 294, ftr | 493, ftr | 611, ftr | 1.70, ftr | 2.86, ftr | 3.54, ftr |

Example 46

Polyester of Example 6 was evaluated with Isocyanate Pre-Polymer II (13.0% Isocyanate) at a mix ratio of Isocyanate Pre-Polymer II:Polyester 6 of 100:70 (molar NCO:OH, 1.31:1) as a solventless system on a PolyType Coater at an application temperature of 40° C. to yield a coating weight indicated in table. The bond strength was examined as a function of curing time and is reported below.

| Laminate Structure | Coating Wt (g/m$^2$) | Bond Strength (g/lin) | | Bond Strength (N/15 mm) | |
|---|---|---|---|---|---|
| | | 1 Day | 7 Day | 1 Day | 7 Day |
| PET/PE | 1.30 | 546, ftr | 583, ftr | 3.16, ftr | 3.38, ftr |
| N/PE | 1.55 | 890, ftr | 1023, ftr | 5.15, ftr | 5.92, ftr |
| MPP/PP | 2.44 | 103, as | 219, ftr | 0.60, as | 1.27, ftr |

Example 47

Polyester of Example 8 was evaluated with Isocyanate Pre-Polymer II (13.0% Isocyanate) at a mix ratio of Isocyanate Pre-Polymer II:Polyester 8 of 100:65 (molar NCO:OH, 1.43:1) as a solventless system on a PolyType Coater at an application temperature of 40° C. to yield a coating weight indicated in table. The bond strength was examined as a function of curing time and is reported below.

| Laminate Structure | Coating Wt (g/m$^2$) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 2.31 | 593, ftr | 843, ftr | 378, ftr | 3.43, ftr | 4.88, ftr | 2.19, ftr |
| PP/PE | 2.31 | 913, ftr | 801, ftr | 1476, ftr | 5.29, ftr | 8.55, ftr | 8.55, ftr |
| PP/PP | 2.31 | 686, ftr | 575, ftr | 1542, ftr | 3.97, ftr | 8.93, ftr | 8.93, ftr |

Example 48

Polyester of Example 8 was evaluated with Isocyanate Pre-Polymer II (13.0% Isocyanate) at a mix ratio of Isocyanate Pre-Polymer II:Polyester 8 of 100:75 (molar NCO:OH, 1.24:1) as a solventless system on a PolyType Coater at an application temperature of 40° C. to yield a coating weight indicated in table. The bond strength was examined as a function of curing time and is reported below.

| Laminate Structure | Coating Wt (g/m$^2$) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 1.95 | 375, as | 534, ftr | 241, ftr | 2.17, as | 3.09, ftr | 1.40, ftr |
| PP/PE | 1.95 | 450, ftr | 794, ftr | 238, ftr | 2.61, ftr | 4.60, ftr | 1.38, ftr |
| PP/PP | 1.95 | 350, ftr | 502, ftr | 130, ftr | 2.03, ftr | 2.91, ftr | 0.75, ftr |

Example 49

Polyester of Example 10 was evaluated with Isocyanate Pre-Polymer II (13.0% Isocyanate) at a mix ratio of Isocyanate Pre-Polymer II:Polyester 10 of 100:75 (molar NCO:OH, 1.28:1) as a solventless system on a PolyType Coater at an application temperature of 40° C. to yield a coating weight indicated in table. The bond strength was examined as a function of curing time and is reported below.

| Laminate Structure | Coating Wt (g/m²) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 1.74 | 350, as | 948, ftr | 881, ftr | 2.03, as | 5.49, ftr | 5.10, ftr |
| PP/PE | 1.74 | 500, ftr | 1225, ftr | 1193, ftr | 2.90, ftr | 7.09, ftr | 6.91, ftr |
| PP/PP | 1.74 | 280, as | 432, ftr | 154, ftr | 1.62, as | 2.50, ftr | 0.89, ftr |

Example 50

Polyester of Example 11 was evaluated with Isocyanate Pre-Polymer II (13.0% Isocyanate) at a mix ratio of Isocyanate Pre-Polymer II:Polyester 11 of 100:65 (molar NCO:OH, 1.47:1) as a solventless system on a PolyType Coater at an application temperature of 40° C. to yield a coating weight indicated in table. The bond strength was examined as a function of curing time and is reported below.

| Laminate Structure | Coating Wt (g/m²) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 1.66 | 344, ftr | 340, ftr | 1113, ftr | 1.99, ftr | 1.97, ftr | 6.45, ftr |
| PP/PE | 1.66 | 560, ftr | 888, ftr | 982, ftr | 3.24, ftr | 5.14, ftr | 5.69, ftr |
| PP/PP | 1.66 | 372, ftr | 851, ftr | 525, ftr | 2.15, ftr | 4.93, ftr | 3.04, ftr |

Example 51

Polyester of Example 11 was evaluated with Isocyanate Pre-Polymer II (13.0% Isocyanate) at a mix ratio of Isocyanate Pre-Polymer II:Polyester 11 of 100:70 (molar NCO:OH, 1.36:1) as a solventless system on a PolyType Coater at an application temperature of 40° C. to yield a coating weight indicated in table. The bond strength was examined as a function of curing time and is reported below.

| Laminate Structure | Coating Wt (g/m²) | Bond Strength (g/lin) | | | Bond Strength (N/15 mm) | | |
|---|---|---|---|---|---|---|---|
| | | 1 Day | 7 Day | >24 Hr Water Soak | 1 Day | 7 Day | >24 Hr Water Soak |
| PET/PE | 1.74 | 459, ftr | 415, ftr | 380, ftr | 2.66, ftr | 2.40, ftr | 2.20, ftr |
| PP/PE | 1.74 | 728, ftr | 1090, ftr | 745, ftr | 4.22, ftr | 6.31, ftr | 4.31, ftr |
| PP/PP | 1.74 | 228, ftr | 672, ftr | 459, ftr | 1.32, ftr | 3.89, ftr | 2.66, ftr |

Example 52

Polyester of Example 13 was evaluated with Isocyanate Pre-Polymer II (13.0% Isocyanate) at a mix ratio of Isocyanate Pre-Polymer II Polyester 13 of 100:70 (molar NCO:OH, 1.48:1) as a solventless system on a PolyType Coater at an application temperature of 40° C. to yield a coating weight indicated in table. The bond strength was examined as a function of curing time and is reported below.

| Laminate Structure | Coating Wt (g/m²) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 1.46 | 522, ftr | 626, ftr | 296, ftr | 3.02, ftr | 3.63, ftr | 1.71, ftr |
| N/PE | 1.79 | 907, ftr | 948, ftr | 547, ftr | 5.25, ftr | 5.49, ftr | 3.17, ftr |
| MPP/PP | 1.95 | 97, as | 130, as | 7, as | 0.56, as | 0.75, as | 0.04, as |

Example 53

Polyester of Example 15 was evaluated with Isocyanate Pre-Polymer II (13.0% Isocyanate) at a mix ratio of Isocyanate Pre-Polymer II:Polyester 15 of 100:70 (molar NCO:OH, 1.45:1) as a solventless system on a PolyType Coater at an application temperature of 40° C. to yield a coating weight indicated in table. The bond strength was examined as a function of curing time and is reported below.

| Laminate Structure | Coating Wt (g/m²) | Bond Strength (g/lin) | | | Bond Strength (N/15 mm) | | |
|---|---|---|---|---|---|---|---|
| | | 1 Day | 7 Day | After 24 Hr Water Soak | 1 Day | 7 Day | After 24 Hr Water Soak |
| PET/PE | 2.12 | 1071, ftr | 1251, ftr | 1348, ftr | 6.20, ftr | 7.25, ftr | 7.81, ftr |
| N/PE | 1.77 | 943, ftr | 1148, ftr | 532, ftr | 5.46, ftr | 6.65, ftr | 3.08, ftr |
| MPP/PP | 2.07 | 221, ftr | 348, ftr | 41, as | 1.28, ftr | 2.02, ftr | 0.24, as |

Summary Table

| polyol Ex. | Adh. Ex. | Wt rac MA (a) | frac. MA unit/ chain (b) | visc. (25 C.) (cps) (mPa·s) | bond str. 7 Days N/15 mm | Viscosity Stability Pot-Life Data @ 40 C. | |
|---|---|---|---|---|---|---|---|
| | | | | | | Initial viscosity (cps) | viscosity 30 min. (cps) |
| 1 | 17 | 0.2221 | 0.6692 | 14425 | 2.36 (d) | | |
| 2 | 18 | 0.2218 | 0.6686 | 8412 | 5.54 (d) | | |
| 3 | 19 | 0.2217 | 0.6681 | 24000 | 5.93 (d) | | |
| 4 | 23 | 0.1843 | 0.5554 | 8875 | 7.92 (e) | | |
| 5 | 20 | 0.1851 | 0.5579 | 6888 | 2.94 (d) | | |
| 6 | 25 | 0.1352 | 0.4076 | 1600 | 5.61 (e) | 1225 | 3737.5 |
| 7 | 27 | 0.1358 | 0.4092 | 2192 | 7.74 (e) | 1612.5 | 4637.5 |
| 8 | 28 | 0.1724 | 0.5194 | 2262 | 8.21 (e) | 1800 | 5587.5 |
| 9 | 29 | 0.1848 | 0.5570 | 3341 | 1.76 (e) | 2137.5 | 7512.5 |
| 10 | 30 | 0.1725 | 0.5197 | 2680 | 4.26 (e) | 1700 | 5225.0 |
| 11 | 32 | 0.1731 | 0.5216 | 1938 | 3.82 (e) | 1800 | 6012.5 |
| 12 | 34 | 0.1113 | 0.3355 | 1191 | 3.54 (e) | 1100 | 5650.0 |
| 13 | 36 | 0.1354 | 0.4079 | 1364 | 5.90 (e) | 1237.5 | 4100.0 |
| 14 | 38 | 0.1279 | 0.3856 | 860 | 6.25 (e) | 962.5 | 3250.0 |
| 15 | 40 | 0.1356 | 0.4086 | 1310 | 4.85 (e) | 1162.5 | 3600 |
| 16 | 43 | 0.1427 | 0.4302 | 1373 | 4.33 (e) | 1262.5 | 4112.5 |

(a): Wt fraction maleic anhydride (MA) = (g MA/g triglyceride)
(b): Based on a theoretical triglyceride molecular weight of 886
(c): Polyester/Polyethylene - for solvent draw downs/laminations
(d): with Isocyanate Prepolymer 1
(e): with Isocyanate Prepolymer 2

Examples within the scope of the invention are enclosed by the heavier borders. Values not meeting the requirements summarized below are underlined. Example 12 was made according to the method of Clocker, U.S. Pat. No. 2,188,882, Ex. 9, but with a much larger amount of ethylene glycol (15% vs. 6%). Even with the larger amount of diol, the resulting material still did not meet the requirements for bond strength and pot life.

For successful commercial use of the polyester resin (polyol) of this invention, its viscosity at 25° C. must be no greater than 2500 cps (mPA·s). Data in the summary table above clearly show that polyols 1-5 and 9-10 are unacceptable. In addition, when the polyol is formulated in a two-component adhesive and used to bond polyester film to polyethylene film, the 7-day bond strength must be at least 3.75 N/15 mm. This requirement eliminated polyol 12, as well as polyols 1, 5 and 9, which were eliminated previously for high viscosity. The two-component adhesive also needs to have a favorable pot life, i.e., the initial viscosity of the blended components at 40° C. must be no greater than 1650 cps and the viscosity after 30 minutes must be no greater than 5500 cps. The pot life of polyols 1-5 was not tested. Each of polyols 8-12 failed to meet at least one of the pot life criteria. Results presented in the summary table clearly indicate that only the polyols within the scope of the present invention (6, 7, 13, 14, 15 and 16) satisfied all of these requirements. One skilled in the art would not have expected that a critical range of maleic anhydride would exist within which the polyol would be suitable for a two-component adhesive formulation.

The invention claimed is:

1. A polyol comprising a substituent of formula (I)

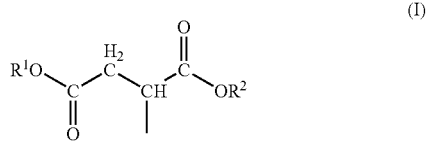

(I)

attached via a carbon-carbon single bond to a saturated carbon atom in a fatty acid hydrocarbyl group; wherein $R^1$ and $R^2$ are esterified residues of aliphatic or cycloaliphatic diols; and wherein the polyol comprises: (i) from 0.37 to 0.44 units of formula (I) per fatty acid hydrocarbyl group, (ii) from 3 to 9 wt % of esterified residues of at least one $C_4$-$C_{12}$ anhydride, $C_4$-$C_{12}$ diacid or $C_4$-$C_{12}$ lactone, not including units of formula (I) attached to a fatty acid hydrocarbyl group, and (iii) 15 to 31 wt % polymerized residues of at least one $C_2$-$C_8$ aliphatic diol; and wherein the polyol has a hydroxyl number from 150 to 195 mg KOH/g.

2. The polyol of claim 1 having 4 to 7 wt % of esterified residues of at least one $C_4$-$C_{12}$ anhydride or $C_4$-$C_{12}$ diacid.

3. The polyol of claim 2 having 4 to 7 wt % of esterified residues of at least one $C_8$-$C_{12}$ aromatic anhydride or diacid.

4. The polyol of claim 3 in which the diol is a $C_2$-$C_4$ aliphatic diol.

* * * * *